(12) United States Patent
Gurewich

(10) Patent No.: US 11,213,574 B2
(45) Date of Patent: Jan. 4, 2022

(54) METHODS FOR SAFE AND EFFECTIVE THROMBOLYSIS USING SEQUENTIAL ADMINISTRATION OF TISSUE PLASMINOGEN ACTIVATOR AND MUTANT PRO-UROKINASE

(71) Applicant: Thrombolytic Science, LLC, Cambridge, MA (US)

(72) Inventor: Victor Gurewich, Cambridge, MA (US)

(73) Assignee: Thrombolytic Science, LLC, Cambridge, MA (US)

( * ) Notice: Subject to any disclaimer, the term of this patent is extended or adjusted under 35 U.S.C. 154(b) by 0 days.

(21) Appl. No.: 15/523,900

(22) PCT Filed: Nov. 3, 2015

(86) PCT No.: PCT/US2015/058878
§ 371 (c)(1),
(2) Date: May 2, 2017

(87) PCT Pub. No.: WO2016/073514
PCT Pub. Date: May 12, 2016

(65) Prior Publication Data
US 2018/0311322 A1 Nov. 1, 2018

Related U.S. Application Data

(60) Provisional application No. 62/074,374, filed on Nov. 3, 2014.

(51) Int. Cl.
*A61K 38/49* (2006.01)
*A61K 38/57* (2006.01)
*A61P 9/10* (2006.01)
*A61K 9/00* (2006.01)

(52) U.S. Cl.
CPC ............ *A61K 38/49* (2013.01); *A61K 9/0019* (2013.01); *A61K 38/57* (2013.01); *A61P 9/10* (2018.01); *C12Y 304/21068* (2013.01); *C12Y 304/21073* (2013.01)

(58) Field of Classification Search
CPC .................................................... A61K 38/49
USPC ...................................................... 424/94.64
See application file for complete search history.

(56) References Cited

U.S. PATENT DOCUMENTS

| 4,381,346 | A | 4/1983 | Syed |
| 5,055,295 | A | 10/1991 | Welzel et al. |
| 5,108,901 | A | 4/1992 | Anderson |
| 5,472,692 | A | 12/1995 | Liu et al. |
| 5,510,330 | A | 4/1996 | Martin et al. |
| 5,569,197 | A | 10/1996 | Helmus et al. |
| 5,626,841 | A | 5/1997 | Gurewich |
| 5,674,192 | A | 10/1997 | Sahatjian et al. |
| 5,759,542 | A | 6/1998 | Gurewich |
| 5,810,767 | A | 9/1998 | Klein |
| 5,866,358 | A | 2/1999 | Brandazza et al. |
| 6,364,893 | B1 | 4/2002 | Shatjian et al. |
| 6,409,716 | B1 | 6/2002 | Shatjian et al. |
| 6,699,230 | B2 | 3/2004 | Jaafar et al. |
| 6,759,042 | B2 | 7/2004 | Higazi |
| 7,070,958 | B2 | 7/2006 | Sarmientos et al. |
| 7,074,401 | B2 | 7/2006 | Gurewich et al. |
| 7,837,992 | B2 | 11/2010 | Gurewich et al. |
| 8,187,592 | B2 | 5/2012 | Gurewich et al. |
| 9,211,317 | B2 | 12/2015 | Liu |
| 2002/0098179 | A1 | 7/2002 | Brearley et al. |
| 2002/0138858 | A1 | 9/2002 | Pinsky |
| 2005/0019863 | A1 | 1/2005 | Sarmientos et al. |
| 2007/0148160 | A1 | 6/2007 | Gurewich et al. |
| 2007/0298024 | A1 | 12/2007 | Gurewich |
| 2009/0226413 | A1 | 9/2009 | Gurewich et al. |
| 2009/0286721 | A1 | 11/2009 | Pan et al. |
| 2010/0196348 | A1 | 8/2010 | Armstrong et al. |
| 2011/0081334 | A1 | 4/2011 | Gurewich et al. |
| 2011/0229454 | A1 | 9/2011 | Liu |
| 2013/0244941 | A1 | 9/2013 | Mannesse et al. |

FOREIGN PATENT DOCUMENTS

| CN | 1377969 | 11/2002 |
| CN | 1142278 | 3/2004 |
| EP | 0 786 257 | 7/2003 |
| EP | 1 615 612 | 1/2011 |
| GB | 2197195 | 5/1988 |
| WO | WO 2016/073514 | 4/2011 |

OTHER PUBLICATIONS

Zarich et al, Sequential Combination Thrombolytic Therapy for Acute Myocardial Infarction: Results of the Pro-Urokinase and t-PA Enhancement of Thrombolysis (PATENT) Trial. J Am Coll Cardiol 1995;26:374-9.*
Liu et al, Prourokinase Mutant That Induces Highly Effective Clot Lysis Without Interfering With Hemostasis. Circ Res. 2002;90:757-763.*
NHLB Institute of the NIH, Symptoms of Stroke. 2014a.*
NHLB Institute of the NIH, Symptoms of Myocardial Infarction. 2014b.*
Zarich et al, Sequential Combination Thrombolytic Therapy for Acute Myocardial Infarction: Results of the Pro-Urokinase and t-PA Enhancement of Thrombolysis (PATENT) Trial. JACC vol. 26, No. Aug. 2, 1995:374-9.*
Gurewich et al, Recombinant human C1-inhibitor prevents non-specific proteolysis by mutant pro-urokinase during optimal fibrinolysis. Thromb Haemost 2009; 102: 279-286.*

(Continued)

*Primary Examiner* — Sheridan Swope
(74) *Attorney, Agent, or Firm* — Fish & Richardson P.C.

(57) ABSTRACT

Provided herein are methods for safe and effective thrombolysis in therapy for human subjects with symptoms of a potential stroke or acute myocardial infarction ("AMI") using a sequential administration of a low dose bolus of human tissue plasminogen activator ("tPA") followed by an infusion of a mutant form of human pro-urokinase ("proUK").

8 Claims, 9 Drawing Sheets

Specification includes a Sequence Listing.

(56) References Cited

OTHER PUBLICATIONS

Chen et al, Low-dose Tissue Plasminogen Activator is as Effective as Standard Tissue Plasminogen Activator Administration for the Treatment of Acute Ischemic Stroke. Current Neurovascular Research, 2014, 11, 62-67.*

Eissa et al, Optimizing the management of acute ischaemic stroke: a review of the utilization of intravenous recombinant tissue plasminogen activator (tPA). J Clin Pharm Ther. Dec. 2012;37(6):620-9. Epub Jun. 19, 2012.*

Collen et al, Synergistic effect on thrombolysis of sequential infusion of tissue-type plasminogen activator (t-PA) single-chain urokinase-type plasminogen activator (scu-PA) and urokinase in the rabbit jugular vein thrombosis model. Thromb Haemost. Oct. 28, 1987;58(3):943-6.*

Patrick et al, User-friendly algorithms for estimating completeness and diversity in randomized protein-encoding libraries. Protein Eng. Jun. 2003;16(6):451-7.*

Robinson et al, Latex D-dimer Signal in In Situ Femoral Vein Thrombus in Swine and Effect of Minidose Exogenous Tissue Plasminogen Activator Bolus. (CHEST 2005; 127:622-629).*

Armstrong et al., "Fibrinolysis for acute myocardial infarction: the future is here and now," Circulation, May 27, 2003;107: 2533-2537.

Badylak et al., "Simple canine model of arterial thrombosis with endothelial injury suitable for investigation of thrombolytic agents," J. Pharmacological Methods, Jul. 1988;19: 293-304.

Baglin et al., "Discovery and characterization of an antibody directed against exosite 1 of thrombin," J Thrommb Haemos, 2016;14:137-142.

Barnwell et al., "Safety and efficacy of delayed intraaterial urokinase therapy with mechanical clot disruption for thromboembolic stroke," Am J Neuroradiology, 1994;15(10):1817-1822.

Bennett et al., "Activation of the complement system by recombinant tissue plasminogen activator," J Amer Coll Cardiol., Sep. 1987;10: 627-632.

Brooks et al., "CHARMM: A Program for Macromolecular Energy, Minimization, and Dynamics Calculations," J. Comp. Chem., 1983;4:187-217.

Bugge et al., "Urokinase-type plasminogen activator is effective in fibrin clearance in the absence of its receptor or tissue-type plasminogen activator," Proc Natl Acad Sci USA, 1996; 93:5899-5904.

De Zwaan et al. "Continuous 48-h C1-inhibitor treatment, following reperfusion therapy, in patients with acute myocardial nfarction" European Heart Journal, 2002;23:1670-1677.

Decision on Appeal in U.S. Appl. No. 11/447,455, dated Aug. 25, 2011, 13 pages.

Dmitry et al., "Rearrangements of the fibrin network and spatial distribution of fibrinolytic components during plasma clot lysis," J Biol Chem., 1996;271: 2133-2138.

Eldering et al., "Expression of Functional Human C1 Inhibitor in COS Cells," The Journal of Biological Chemistiy, 1988;263(24), Issue of Aug. 25:11776-11779.

Ellis et al., "Facilitated PCI in Patients with ST-Elevation Myocardial Infarction," New English Journal of Medicine, 358(21):2205-2217 (2008).

Fennerty et al., "Hemorrhagic complications of thrombolytic therapy in the treatment of myocardial infarction and venous thromboembolism," Chest., 1989;95: 88S-97S.

Final Office Action in U.S. Appl. No. 11/447,455, dated Apr. 22, 2008, 11 pages.

Final Office Action in U.S. Appl. No. 11/447,455, dated Aug. 6, 2009, 9 pages.

Final Office Action in U.S. Appl. No. 11/447,455, dated Jan. 28, 2009, 10 pages.

Final Office Action in U.S. Appl. No. 11/447,455, dated Mar. 15, 2010, 9 pages.

Grau et al. "Fibrinolytic activity of normal human blood monocytes," Thromb Res, 1989;53:145-162.

Gregorek et al. "Concentration sf C1 Inhibitor in Sera of Healthy Blood Donors as Studied by Immunoenzymatic Assay" Complement and Inflammation 8(5-6), 1991;310-312 (abstract).

Gurewich et al., "Effective and Fibrin-specific Clot Lysis by a Zymogen Precursor Form of Urokinase (Pro-urokinase)", J. Clin. Invest. 1984;73:1731-1739.

Gurewich et al., "Recombinant human C1-inhibitor prevents non-specific proteolysis by mutant pro-urokinase during optimal fibrinolysis. Thrombosis and haemostasis," Thromb Haemost, 2009;102:279-286.

Gurewich et al., "Synergism of tissue-type plasminogen activator (t-PA) and single-chain urokinase-type plasminogen activator (scu-PA) on clot lysis in vitro and a mechanism for this effect," Thromb Haemost, 1987;57:372-378.

Gurewich et al., "The selective uptake of high molecular weight urokinase-type plasminogen activator by human platelets," Fibrinolysis, 1995;9:188-195.

Gurewich et al., "Thrombolysis vs. bleeding from hemostatic sites by a prourokinase mutant compared with tissue plasminogen activator," J Thromb Haemost., Jul. 2006;4:1559-65.

Gurewich et al., New Therapeutic Agents in Thronmbosis and Thrombolysis, 2nd edition, chap 36, "A mutant form of prourokinase that spares hemostatic fibrin," A.A. Sasaara and J. Loscalzo, eds., Marcel Dekker, Inc, NY, pp. 583-592, 2003, rec'd at the NIH Natl Library of Medicine, Bethesda, MD on Dec. 10, 2002.

Gurewich, "Therapeutic fibrinolysis. How efficacy and safety can be improved," J Am Coll Cardiol., 2016;68:2099-2106.

Harpel et al., "Tissue plasminogen activator and urokinase mediate the binding of Glu-plasminogen to plasma fibrin I. Evidence for new binding sites in plasmin-degraded fibrin I," J Biol Chem, Apr. 10, 1985;260: 4432-4440.

Harris, "Second-Generation Plasminogen Activators," Protein Engineering, 1987;1(6):449-458.

Heckel et al., "Prediction of the three-dimensional structure of the enzymatic domain oft-PA", J. Cornn. Aided Mol. Des., 1988;2:7-14.

Hermann et al., "Facilitation of early percutaneous coronary intervention after reteplase with or without abciximab in acute myocardial infarction. Results from SPEED (GUSTO-4 pilot) trial," J Am Coll Cardiol, 36(5):1489-1496 (2000).

Hoylaerts et al., "Kinetics of the activation of plasminogen by human tissue plasminogen activator. Role of fibrin," J Biol Chem., Mar. 1982;257: 2912-2919.

Huisman et al., "On the role of C1-inhibitor as inhibitor of tissue-type plasminogen activator in human plasma," Thromb Haemost., Mar. 1995;73: 466-471.

International Preliminary Report on Patentability in International Application No. PCT/US2015/58878, dated May 9, 2017, 9 pages.

International Search Report and Written Opinion in International Application No. PCT/US2004/11840, dated Apr. 5, 2005, 9 pages [previously cited as: Notification of Transmittal of the International Search Report and Written Opinion of the International Searching Authority (and including the International Search Report and Written Opinion of the International Searching Authority) dated Apr. 5, 2005].

Kunkel, "Rapid and efficient site-specific mutagenesis without phenotype selection," Proc. Natl. Acad. Sci., Jan. 1985;82:488-492.

Lenich et al., "Thrombin Stimulation of Platelets Induces Plasminogen Activation Mediated by Endogenous Urokinase-Type Plasminogen Activator," Blood, 90:3579-86 (Nov. 1997).

Liu et al., "A transitional state of pro-urokinase which has a higher catalytic efficiency against glu-plasminogen than urokinase," J Biol Chem., 1992;267:15289-15292.

Liu et al., "A comparative study of the promotion of tissue plasminogen activator and pro-urokinase-induced plasminogen activation by fragments D and E-2 of fibrin," J Clin Invest., Dec. 1991;88:2012-2017.

Liu et al., "A Site-Directed Mutagenesis of Pro-Urokinase at the Flexiblr Loop Region of Active Domain", Advances in Gene Technology: Protein Engineering and Beyond, Jan. 1, 1993, 6(Issue Supplment):45 (Abstract Only).

Liu et al., "A site-directed mutagenesis of pro-urokinase which substantially reduces its intrinsic activity," Biochemistiy, Nov. 12, 1996;35: 14070-14076.

(56) References Cited

OTHER PUBLICATIONS

Liu et al., "Fragment E-2 from fibrin substantially enhances pro-urokinase-induced Glu-plasminogen activation. A kinetic study using the plasmin-resistant mutant pro-urokinase Ala-158-rpro-UK," Biochemistiy, Jul. 14, 1992;31: 6311-6317.
Liu et al., "Inactivation of the Intrinsic Activity of Pro-urokinase by Diisoprophyl Fluorophosphate Is Reversible", The Journal of Biological Chemistiy, vol. 210(15), na2es 8408-8410 (1995).
Liu et al., "Prourokinase Mutant That Induces Highly Effective Cost Lysis Without Interfering With Hemostatsis", Circ Res. Apr. 19, 2002; 90: 757-763.
Liu et al., "The Kinetics of Plasminogen Activation by Thrombin-Cleaved Pro-Urokinase and Promotion of its Activity by Fibrin Fragment E-2 and by Tissue Plasminogen Activator," Blood, 81:980-987 (Feb. 1993).
Loscalzo et al., "Clot-Selective Coronary Thrombolysis with Pro-urokinase," Circulation, Apr. 1989, 79(4):776-782.
Mandel et al., "Calcium-dependent bacteriophage DNA infection," J. Mol. Biol., Oct. 14, 1970;53:159-162.
Meyer, "Randomised double-blind trial of recombinant pro-urokinase against streptokinase in acute myocardial infarction, PRIMI Trial Study Group," Lancet 1989;1:863-867.
Michels et al., "A double-blind multicenter comparison of the efficacy and safety ofsaruplase andurokinase in thetreatment ofacutemyocardialinfarction: Report of the SUTAMI study group," Thromb. Thrombolysis, 1995; 2:117-124.
Montoney et al., "Comparison of the bleeding potential of vampire bat salivary plasminogen activator versus tissue plasminogen activator in an experimental rabbit model," Circulation, Mar. 1, 1995; 91:1540-1544.
Murano et al., "The inhibition of high and low molecular weight urokinase in plasma," Blood, Mar. 1980; 55: 430-436.
Nallamothu et al., "Time to Treatment in Primary Percutaneous Coronary Intervention," New England Journal of Medicine, 357(16):1631-1638 (2007).
Nienaber et al., "Conformational Similarities between One-Chain and Two-Chain Tissue Plasm.inogen Activator (t-PA): Implications to the Activation Mechanism on One-Chain t-PA", Biochemistiy, vol. 31, pp. 3852-3861 (1992).
Ning et al., "Prourokinase Mutant That Induces Highly Effective Clot Lysis Without Interfering With Hemostasis," Circulation Research, vol. 90 (7), pp. 757-763 (2002).
Non-Final Office Action in U.S. Appl. No. 11/447,455, dated Apr. 9, 2009, 7 pages.
Non-Final Office Action in U.S. Appl. No. 11/447,455, dated Aug. 1, 2008, 12 pages.
Non-Final Office Action in U.S. Appl. No. 11/447,455, dated Nov. 2, 2009, 8 pages.
Non-Final Office Action in U.S. Appl. No. 11/447,455, dated Nov. 30, 2011, 14 pages.
Orsini et al., "Efficient renaturation and fibrinolytic properties of prourokinase and a deletion mutant expressed in *Escherichia coli* as inclusion bodies", Eur. J. Biochem., vol. 195, pp. 691-697 (1991).
Owen et al., "Thrombolytic therapy with tissue plasminogen activator or streptokinase induces transient thrombin activity," Blood., Aug. 1988;72: 616-620.
Pannell et al., "A comparison of the rates of clot lysis in a plasma milieu induced by tissue plasminogen activator (t-PA) and rec-prourokinase: evidence that t-PA has a more restricted mode of action," Fibrinolysis, 1992;6:1-5.
Pannell et al., "Activation of Plasminogen by Single-Chain Urokinase or by Two-chain Urokinase—A Demonstration That Single-Chain Urokinase Has a Low Catalytic Activity (Pro-Urokinase)", Blood., Jan. 1987;69:22-26.
Pannell et al., "Complementary modes of action of tissue-type plasminogen activator and pro-urokinase by which their synergistic effect on clot lysis may be explained," J Clin Invest., Mar. 1988;81: 853-859.
Pannell et al., "Pro-urokinase: a study of its stability in plasma and of a mechanism for its selective fibrinolytic effect," Blood., May 1, 1986;67:1215-1223.
Pannell et al., "Highly effective fibrinolysis by a sequential synergistic combination of mini-dose tPA plus low-dose mutant pro Uk," PLOS One, 2015;10:1-15.
Pannell, "C1-inhibitor prevents non-specific plasminogen activation by a prourokinase mutant without impeding fibrin-specific fibrinolysis," J Thromb Haemost, 2007;5:1047-1054.
Parsons et al., "Diffusion- and perfusion-weighted MRI response to thrombolysis in stroke," Ann Neurol 51(1):28-37 (2001).
Petersen, "Kinetics of reciprocal pro-urokinase/plasminogen activation. Stimulation by a template formed by the urokinase receptor bound to poly (D-lysine)," Eur J Biochem, 1997;245:316-323.
Peterson et al., "Quenching of the Amidolytic Activity of One-Chain Tissue-Type Plasminogen Activator by Mutation ofLysine-416", Biochem., vol. 29, pp. 3451-3457 (1990).
Rao et al., "Thrombolysis in myocardial infarction (TIMI) trial—Phase I: Hemorrhagic manifestations and changes in plasma fibrinogen and the fibrinolytic system in patients treated with recombinant tissue plasminogen activator and stretokinase," J Amer Coll Cardiol., Jan. 1988;11:1-11.
Rapold et al., "Requirement of heparin for arterial and venous thrombolysis with recombinant tissue-type plasminogen activator," Blood, Mar. 1, 1991;77:1020-1024.
Ross et al., "The effects of tissue plasminogen activator, streptokinase, or both on coronary-artery patency, ventricular function, and survival after acute myocardial infarction," N Engl J Med, 1993;329:1615-1622.
Singh et al., "Failure of thrombus to resolve in urokinase-type plasminogen activator gene-knockout mice: rescue by normal bone marrow-derived cells," Circulation, 2003;107:869-875.
Smith, "In vitro mutagenesis," Am. Rev. Genet, 1985;19:423-462.
Stone, "Facilitated angioplasty: paradise lost," The Lancet, 367:543-546 (2006).
Studier et al., "Use of bacteriophage T7 RNA polymerase to direct selective high-level expression of cloned genes," J. Mol. Biol., May 5, 1986;189:113-130.
Studier et al., "Use of T7 RNA polymerase to direct expression of cloned genes," Meth. Ezymol, 1990;185:60-89.
Suenson et al., "Initial plasmin-degradation of fibrin as the basis of a positive feed-back mechanism in fibrinolysis," Eur J Biochem., 1984;140: 513-522.
Sun et al., "Identification of a flexible loop region (297-313) of urokinase-type plasminogen activator, which helps determine its catalytic activity," J Biol Chem., Sep. 19, 1997;272:23818-23823.
Swaim et al., "Fibringoen Assay," Clin. Chem., 13:1026-1028 (Nov. 1967).
Tebbe et al., "Randomized, double-blind study comparing saruplase with streptokinase therapy in acute myocardial infarction: the COMPASS equivalence trial.," J. Am. Coll. Cardiol., 1998;31:487-493.
Vaughan et al., "Urokinase binds to platelets through a specific saturable, low affinity mechanism," Fibrinolysis, 1990;4:141.
Verde et al., "Identification and primary sequence of an unspliced human urokinase poly(A)$^+$ RNA", Proc. Natl. Acad. Sci., 1984;81:4727-4731.
Verheught, "Lyse now, stent later: the grace of GRACIA," Lancet, 364:1014-1015, 2004.
Voskuilen et al., "Fibrinogen lysine residue A$\alpha$157 plays a crucial role in the fibrin-induced acceleration of plasminogen activation, catalyzed by tissue-type plasminogen activator," J Biol Chem, 1987;262(13);5944-5946.
Wang et al., "Bovine chymotrypsinogen A X-ray crystal structure analysis and refinement of a new ciystal form at 1.8 A resolution," J. Mol. Biol., 1985;185:595-624.
Weaver et al., "Prourokinase Study Group. New recombinant glycosylated prourokinase for treatment of patients with acute myocardial infarction," J. Am. Coll. Cardiol., 1994;241: 242-1248.
Yuming et al., "High-level Expression and Purification of Human Pro-UK cDNA in *Escherichia coli*," Chinese Journal of Biotechnology, 1997;13(4):233-8.

(56) References Cited

OTHER PUBLICATIONS

Zarich et al., "Sequential combination thrombolytic therapy for acute myocardial infarction: results of the pro-urokinase and t-PA enhancement of thrombolysis (PATENT) trial," J Am Coll Cardio, 1995;26:374-379.
Gurewich, "Experiences With Pro-Urokinase and Potentiation of Its Fibrinolytic Effect by Urokinase and by Tissue Plasminogen Activator," Journal of the American College of Cardiology 10: 16B-21B (1987).
International Search Report and Written Opinion dated Feb. 17, 2016 in international application No. PCT/US2015/58878, 11 pgs.
European Search Report in European Patent Application No. 15856204.1, dated Jul. 6, 2018, 10 pages.
Smith, "The influence of Bolus to Infusion Delays on Plasma Tissue Plasminogen Activator Levels," International Journal of Stroke, 9(7):939-942 (Oct. 2014).
EA Office Action in Eurasian Appln. No. 201790969, dated Oct. 2, 2018, 4 pages (with English translation).
EP Office Action in European Appln. No. 15856204.1, dated Mar. 11, 2019, 3 pages.
JP Office Action in Japanese Appln. No. 2017-543288, dated Jun. 18, 2019, 6 pages (with English translation).
IN Office Action in Indian Appln. No. 201747019519, dated Jul. 1, 2020, 6 pages.
Braunwald, et al., "Announcement of protocol change in thrombolysis in myocardial infarction trial," J. Amer. Coll. Cardiol., 1987, 9(2):467.
Grossbard, "Genentech experience with rt-PA (activase)," J. Amer. Coll. Cardiol., 1987, 9(2):467.
Gulba, et al., "Increased thrombin levels during thrombolytic therapy in acute myocardial infarction," Circulation, 1991, 83:937-944.
Gulba, et al., "Thrombin/antithrombin-III complex level as early predictor of reocclusion after successful thrombolysis," Lancet, 1988, 9(2):97.
Gurewich, "Coronary rethrombosis after successful thrombolysis," Circulation, 1993, 87:1759-1761.

PCT International Preliminary Report on Patentability in International Appln. No. PCT/US2018/037855, dated Dec. 17, 2019, 8 pages.
PCT International Search Report and Written Opinion dated Sep. 11, 2018 in international application No. PCT/US2018/037855, 14 pgs.
Rapold et al., "Plasma levels of plasminogen activator inhibitor type 1, beta-thromboglobulin, and fibrinopeptide A before, during, and after treatment of acute myocardial infarction with alteplase," Blood, 1991, 78(6):1490-1495.
Verheugt et al., "Reocclusion: the flip side of coronary thrombolysis," Journal of the American College of Cardiology, Mar. 15, 1996, 27(4):766-773.
CN Office Action in Chinese Appln. No. 201580058489.0, dated Jun. 9, 2020, 25 pages (with English translation).
JP Office Action in Japanese Appln. No. 2017-543288, dated Apr. 14, 2020, 10 pages (with English translation).
BR Office Action in Brazilian Appln. No. BR112017008749-9, dated Jul. 8, 2020, 6 pages (with English translation).
EP Extended European Search Report in European Appln. No. 20158876.1, dated Jul. 24, 2020, 15 pages.
CN Office Action in Chinese Appln. No. 201580058489.0, dated Dec. 2, 2020, 22 pages (with English translation).
Gurewich et al., "Fibrinolytic mechanisms of tPA, prouPA, mutant prouPA and their implications for therapeutic thrombolysis," Cardiovascular Engineering and Technology, Dec. 1, 2013, 4(4):328-38.
Gurewich, "Why so little progress in therapeutic thrombolysis? The current state of the art and prospects for improvement," Journal of Thrombosis and Thrombolysis, Nov. 2015, 40(4):480-7.
Hackett et al., "Effectiveness and safety of a single intravenous bolus injection of tissue-type plasminogen activator in acute myocardial infarction," The American Journal of Cardiology, Jun. 1, 1992, 69(17):1393-8.
Verstraete et al., "Bolus alteplase," The Lancet, Oct. 21, 1989, 334(8669):989-90.

* cited by examiner

METHODS FOR SAFE AND EFFECTIVE THROMBOLYSIS USING SEQUENTIAL ADMINISTRATION OF TISSUE PLASMINOGEN ACTIVATOR AND MUTANT PRO-UROKINASE

CLAIM OF PRIORITY

This application is the National Stage under 371 of International Application No. PCT/US2015/058878, filed on Nov. 3, 2015, which claims the benefit of U.S. Provisional Application Ser. No. 62/074,374, filed on Nov. 3, 2014. The entire contents of the foregoing applications are incorporated herein by reference.

SEQUENCE LISTING

The instant application contains a Sequence Listing, which has been submitted electronically in ASCII format and is hereby incorporated by reference in its entirety. Said ASCII copy, created on Oct. 26, 2020, is named Sequence Listing and is 4KB in size.

TECHNICAL FIELD

This invention relates to methods and compositions for safe and effective thrombolysis.

BACKGROUND

Thrombosis occurs when a blood clot (thrombus) forms inside a blood vessel and obstructs the flow of blood through the circulatory system. When a blood vessel is injured, the body uses platelets and fibrin to form a blood clot to seal injured vessels and prevent blood loss. This process is called hemostasis. Even when a blood vessel is not injured, blood clots may form in the body under certain circumstances. Blood clots consist largely of aggregated platelets and a mesh of cross-linked fibrin, which is a natural polymer of fibrinogen in the blood. When a thrombus is large enough to reduce the blood flow to a tissue, hypoxia or anoxia can occur, leading to tissue damage or even tissue death. Depending on the location in the arterial system, i.e., heart, brain, or leg, a thrombus can trigger heart attack, stroke, or peripheral gangrene. In the venous circulation the same process can cause thrombophlebitis (deep vein thrombosis) or a pulmonary embolism. Together, these cardiovascular diseases constitute the leading causes of death and disability in industrialized countries.

Thrombolysis mainly involves the use of thrombolytic drugs to dissolve the disease-causing blood clot and restore blood flow. Thrombolytic drugs such as tPA and its derivatives in current use function by activating the proenzyme plasminogen to the protease plasmin, which degrades the fibrin mesh in the blood clot and makes the clot soluble, thus restoring blood flow through occluded blood vessels. However, the present thrombolytic drugs also induce degradation of hemostatic fibrin that seals wounds, and generate plasmin in plasma which degrades three clotting factors, fibrinogen, factor V, and factor VII (hemophilic factor). Thus, current thrombolytic therapy carries the risk of causing bleeding from hemophilia-like side effects or from the degradation of hemostatic fibrin. This imposes serious limitations on the number of patients eligible for treatment and limits the dose of thrombolytic that can be used. As a result, only about 5% of patients with stroke receive treatment and the efficacy of this treatment is limited.

A stroke can be caused either by a blood clot or a bleeding vessel in the brain. However, properly diagnosing the specific cause of a stroke requires a CT scan or MRI, which can delay treatment if not immediately available. Absent such a proper diagnosis, it can be very dangerous to administer a clot dissolving agent, such as tissue plasminogen activator ("tPA"), if the cause happens to be a bleed rather than a blood clot, as the results of administering tPA or other thrombolytic agent to a patient who has had a brain bleed can be fatal.

SUMMARY

The present disclosure is based, at least in part, on the discovery that the distinct and different specificities of tPA and prourokinase mutant ("proUK mutant or "mproUK") means that small doses of each in combination induces thrombolysis that is faster and safer, i.e., more specific and with lower incidence of bleeding complications, e.g., for treating stoke or acute myocardial infarction ("AMI"), than is possible using either one alone (monotherapy) with high doses that achieve a maximum blood clot lysis rate, but with a high risk of bleeding complications.

The mproUK can comprise a substitution of histidine for lysine at amino acid position 300 (Lys300→His) of pro-urokinase (SEQ ID NO:1), referred to herein as "MS." mproUK, like proUK, is a proenzyme, i.e., the inactive precursor of the active enzyme. It differs from pro UK in that its enzymatic form mutant urokinase or mUK, unlike urokinase (UK), is inhibited by a plasma inhibitor, CI-inhibitor, which additionally to the lower doses necessary, helps to reduce the bleeding side effects seen with pro-UK, which are due to UK for which there is insufficient inhibitor (plasminogen activator inhibitor-1, PAI-1) in the plasma.

For patients with stroke or AMI, the time needed for thrombolysis and reperfusion is critical to clinical outcome and survival rate. This means that treatment must be safe enough to be given outside the hospital without preliminary diagnostic testing. However, this is possible only if the hemorrhagic risk is greatly reduced or eliminated, as is the case with the new methods described herein including the administration of a mini-dose of tPA (e.g., a bolus of less than 5.0 mg, e.g., less than or equal to 4.5 mg, 4.0 mg, 3.5 mg, 3.0 mg, 2.5 mg, or 2.0 mg) and low dose of mproUK (e.g., an infusion over 60 to 90 minutes (e.g., 60, 70, 80, or 90 minutes) at a rate of 60 to 120 mg/hour, e.g., 60 to 90 mg/hour, e.g., 60, 65, 70, 75, 80, 85, or 90 mg/hour) in combination.

If the endogenous concentration of C1-inhibitor is insufficient in a given subject, it can be supplemented in the new methods by administering an effective amount of a C1-inhibitor, e.g., a commercially available C1-inhibitor such as CINRYZE®, CETOR®, BERINERT®, and RUCONEST®. The C1-inhibitor is an additional precaution in case some conversion of mproUK to mutant UK occurs, but may not be necessary due to the low dose of mproUK required and the fact that C1-inhibitor is an acute phase reactant, which is automatically elevated by the body immediately after a heart attack or stroke.

Provided herein in a first aspect are methods of treating a subject, e.g., a human patient, with symptoms of a stroke or an acute myocardial infarction (AMI) at a maximum rate of blood clot lysis and with minimal associated hemorrhagic side effects, the methods include (a) identifying a subject who potentially had a stroke or AMI by observing one or more symptoms of a stroke or AMI without determining the cause of the stroke; and (b) administering to the subject a bolus of a first composition including a mini-dose, i.e., less than 5 mg, of tissue plasminogen activator (tPA), e.g., 2.0, 2.5, 3.0, 3.5, 4.0, or 4.5 mg of tPA, followed by an intravenous infusion of a second composition including a low dose of pro-urokinase mutant (mproUK) infused over 60 to 90 minutes, e.g., 60, 65, 70, 75, 80, 85, or 90 minutes, at a low dosage rate of 60 to 120 mg, e.g., 60, 70, 75, 80, 85, 90, 100, or 120 mg/hour; wherein a maximum clot lysis rate is achieved with minimal associated hemorrhagic side effects.

In some embodiments of these methods the minimal associated hemorrhagic side effects can be determined as a level of fibrinogen degradation in the subject's blood of less than about 30 percent, e.g., less than 27.5%, 25%, 22.5%, or 20% fibrinogen degradation (whereas fibrinogen degradation is about 50 to 80% with monotherapy by either composition alone). In some embodiments, the maximum clot lysis rate is indicated as having been achieved by a Thrombolysis In Myocardial Infarction (TIMI) score of 2 or higher. In other embodiments, the maximum clot lysis rate is indicated as having been achieved by a lysis of about 50% of the mass of at least one clot in the subject achieved within 75 minutes, e.g., within 70, 60, 50, 40, 04 30 minutes.

In these methods, the pro-urokinase mutant can include a substitution of histidine for lysine at amino acid position 300 (Lys300→His) of pro-urokinase. The methods can include starting administration of the second composition within five, 10, or 15 minutes after the administration of the first composition. In some embodiments, the first composition and the second composition together lyse 50% of a mass of at least one blood clot in the subject in less than one hour.

In certain embodiments, the methods can further include administering to the subject a third composition including a bolus of C1-inhibitor. The third composition can be administered to the subject before or at about the same time, e.g., within 5 minutes, of the administration of the second composition. In certain embodiments, the third composition is administered in an amount sufficient to establish a concentration of C1-inhibitor that is about 500-750 µg/mL in the subject's blood. In some embodiments, the third composition is a bolus of 500-1500 mg of C1-inhibitor.

In some of these methods the first composition and the second composition together lyse the blood clots in the presence of the C1-inhibitor with less than 30% fibrinogen degradation when compared to monotherapy by either tPA or pro-urokinase alone.

In another aspect, the disclosure provides kits that include a first composition in a first container including 2-5 mg of tissue plasminogen activator (tPA); and a second composition in a second container including 60-120 mg of a pro-urokinase mutant (mproUK) having a substitution of histidine for lysine at amino acid position 300 (Lys300→His) of pro-urokinase. In these kits, the first composition can be formulated suitable for administration as a bolus and/or the second composition can be formulated suitable for intravenous infusion. In certain embodiments, the kits further include a third composition including 500-1500 mg of C1-inhibitor, e.g., formulated suitable for administration as a bolus.

In another aspect, the disclosure provides compositions for use in any of the methods described herein. In certain embodiments, the compositions are for use in treating a subject with symptoms of a stroke or acute myocardial infarction (AMI) at a maximum rate of clot lysis and with minimal associated hemorrhagic side effects. These compositions include a first composition including less than 5 mg of tissue plasminogen activator (tPA), wherein the first composition is or is prepared to be administered to a subject in a dosage regime of a bolus; and a second composition including a pro-urokinase mutant (mproUK), wherein the second composition is or is prepared to be administered to a subject by an intravenous infusion in a dosage regime of 60 to 120 mg/hour for 60 to 90 minutes following the administration of the first composition; wherein the subject is identified as potentially having had a stroke or AMI by observing one or more symptoms of a stroke or AMI without determining the cause of the stroke prior to administering the first composition; and wherein a maximum clot lysis rate is achieved with minimal associated hemorrhagic side effects. These compositions can include all of the features and elements described herein.

The term "treatment" or "therapeutic treatment" means the administration of one or more pharmaceutical agents to a subject or the performance of a medical procedure on the body of a subject. The term therapeutic treatment also includes an adjustment (e.g., increase or decrease) in the dose or frequency of one or more pharmaceutical agents that a subject can be taking, the administration of one or more new pharmaceutical agents to the subject, or the removal of one or more pharmaceutical agents from the subject's treatment plan.

As used herein, a "subject" or "patient" is a human.

An "effective amount" used herein is an amount sufficient to achieve thrombolysis without causing significant hemorrhagic or hemophilia-like side effects. An effective amount can be administered in one or more administrations, applications, or dosages. A therapeutically effective amount of a pharmaceutical composition (i.e., an effective dosage) depends on the pharmaceutical composition selected.

The "maximum lysis rate" of blood clots is defined herein as a rate of lysis of blood clots at least as fast as what can be achieved by monotherapy with tPA, proUK or mproUK at a maximally effective dosage (i.e., a dose of the drug at which no faster clot lysis can be achieved by adding additional drug, e.g., a plateau in the clot lysis rate is shown at the maximally effective dosage) without any associated hemorrhagic side effects. It is important to note that the maximum lysis rate achieved using monotherapy, e.g., with tPA or M5, would cause significant bleeding in a patient, as indicated, for example, by a level of fibrinogen degradation of greater than 30%. Surprisingly, the present therapeutic methods achieve the maximum lysis rate without hemorrhagic side effects, which can be indicated by a fibrinogen degradation level of less than 30%, which would not be associated with excess bleeding and would be clinically acceptable.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF THE DRAWINGS

The time used by tPA to lyse 50% of the plasma clots at a saturated dose of 3 µg/ml is 60 minutes.

FIG. 2A is a line graph showing the lysis of fluorescein-labeled plasma clots by mproUK (M5) at three doses: 10, 12.5, or 15 µg/ml. The time used by M5 to lyse 50% of the plasma clots at a saturated dose is 50 minutes. FIG. 2C is a line graph showing the time used by mproUK (M5) to lyse fluorescein-labeled plasma clots was unaffected by the C1-inhibitor (750 µg/ml). FIG. 2D is a bar graph showing fibrinogenolysis by M5 was prevented by the C1-inhibitor (750 µg/ml).

DETAILED DESCRIPTION

Figure 1A:
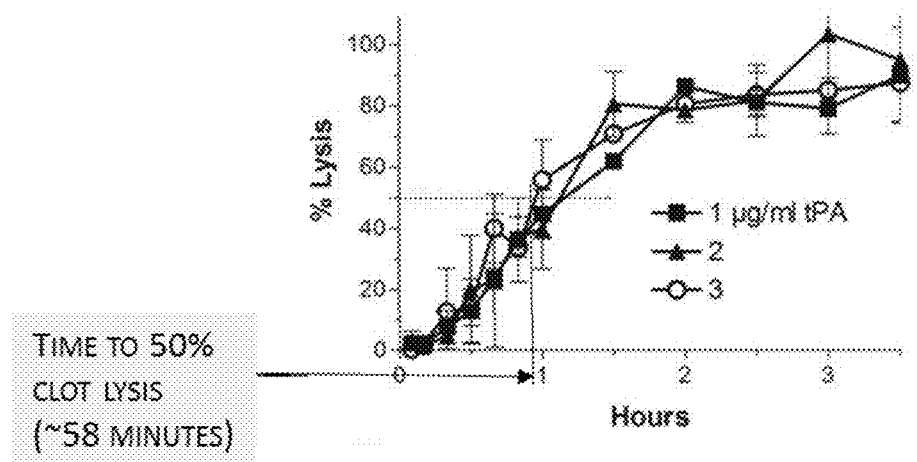
FIG. 1A is a line graph showing the lysis of fluorescein-labeled plasma clots by tPA at three doses: 1, 2, or 3 µg/ml.

The present disclosure is based, at least in part, on the discovery that thrombolysis can be achieved at a maximum clot lysis rate to achieve increased blood flow, e.g., at a Thrombolysis In Myocardial Infarction (TIMI) score of 2 or better within about 75 minutes and without the expected hemorrhagic risk by administering a combination of a mini-dose of tissue plasminogen activator (tPA) and a low dose of pro-urokinase mutant ("pro-UK mutant" or "mproUK"), for example, a mproUK that comprises a substitution of histidine for lysine at amino acid position 300 (Lys300→His) of pro-urokinase, referred to herein as "M5." For patients with stroke or acute myocardial infarction, the time needed for thrombolysis and reperfusion is critical to clinical outcome and survival rate. To make this possible, treatment must also be safe enough so that patients can be treated before hospitalization. Provided herein are methods of treating a subject who potentially had a stroke or acute myocardial infarction.

These methods can be used to treat patients with symptoms of stroke or acute myocardial infarction without the delay caused by time-consuming diagnostic procedures, thereby enhancing the chances of better clinical outcome and survival rate for those patients. Since fibrinolysis can be achieved with mini-doses of tPA and low doses of mproUK in the combination, non-specific activation of plasminogen and the hemophiliac-like side effects associated with high dose plasminogen activator regimens can be reduced to minimal levels while still achieving a maximum clot lysis rate. Also provided herein are kits that include a first composition comprising tPA and a second composition comprising mproUK, for use in the methods described herein.

Blood clots are lysed in three steps by the protease plasmin, which is the activated form of plasminogen. Step 1: plasminogen present in the blood plasma binds to the intact fibrin clot at a specific binding site on the D-domain that is adjacent to the tPA binding site. tPA activates plasminogen in this so-called "ternary complex", which consists of fibrin, plasminogen, and tPA, and initiates fibrinolysis. Step 2: plasmin cleaves fibrin preferentially after a lysine residue, creating carboxy terminal lysines which represent new plasminogen binding sites. One of these newly created binding sites is a high affinity binding site consisting of three C-terminal lysines in the fibrin E-domain. When plasminogen binds to this site in the fibrin E-domain, it undergoes a special conformational change which enables it to be activated by the intrinsic catalytic activity of pro-UK and mproUK. Step 3: activation of the plasminogen by pro-UK/mproUK is accompanied by reciprocal activation of pro-UK/mproUK by plasmin to the enzyme urokinase (UK)/mUK. UK/mUK then activates the remaining fibrin-bound plasminogen, thereby completing fibrinolysis (see U.S. Pat. Nos. 5,055,295; 5,472,692; 5,626,841; 5,759,542; 7,074,401; 7,837,992; 8,187,592; Pannell, J. Clin. Invest. 81: 853-859, 1988; Zarich, J Am Coll Cardiol 1995; 26: 374-379; Lee, AJNR Am J Neuroradiol 25: 1470-1475, 2004).

The present inventor has discovered how the new combination therapy methods described herein are supported by the steps of fibrinolysis described above. Only tPA can efficiently perform step 1, since only tPA binds to fibrin, forms a ternary, complex with plasminogen and is specifically promoted by intact fibrin or by fibrin fragment D. Pro-UK/mproUK does not bind to fibrin in vivo under normal conditions (i.e., it can bind to fibrin only at very high, non-specific doses). Thus, step 2 can be performed efficiently only by pro-UK/mproUK, because it has a high substrate affinity for the plasminogen confirmation that forms when it binds to the fibrin E-domain of degraded fibrin. Fibrin fragment E has no effect on tPA, which does not bind to this domain, and promotes plasminogen activation only by proUK/mproUK. Thus, step 3 is also promoted only by pro-UK/mproUK, because, when proUK activates plasminogen bound to the fibrin E-domain, there is reciprocal activation of proUK to UK by plasmin and UK completes lysis by activating the remaining fibrin-bound plasminogen (by contrast, tPA undergoes no activation, because its one and two-chain forms have identical activities). The only way tPA can perform steps 2 and 3 is at high non-specific doses that are associated with a high bleeding risk.

The present inventor has discovered that fibrinolysis can be attained with a combination of a mini-dose of tPA (only 2-5% of the standard 100 mg dose) plus a low dose of a mproUK, e.g., M5 (40-50% of the mono-therapy dose) at a maximum rate of clot lysis with a minimal level of fibrinogen degradation of less than about 30% (e.g., less than about 25 or 20%). This tPA-mproUK combination achieves fibrinolysis at a maximum lysis rate that is at least the same as the maximum rate of lysis that can be achieved by monotherapy with either tPA or mproUK at a maximum dose, but with far lower levels of fibrinogen degradation that are safe and clinically acceptable, as no bleeding risks arise at these lower levels, which is not possible with known monotherapies. Thus, the present methods described herein provide thrombolysis that is clearly superior to any alleged synergistic combination, which would not include the newly discovered dual benefits of a maximum blood clot lysis rate with maximum safety for the patient, i.e., minimal associated hemorrhagic side effects.

The "maximum lysis rate" of blood clots is defined herein as a rate of lysis of blood clots at least as fast as what can be achieved by monotherapy with tPA, proUK or mproUK at a maximally effective dosage (i.e., a dose of the drug at which no faster clot lysis can be achieved by adding additional drug, e.g., a plateau in the clot lysis rate is shown at the maximally effective dosage). However, it is important to note that the maximum lysis rate achieved using monotherapy, e.g., with tPA or M5, would cause significant bleeding in a patient, as indicated, for example, by a level of fibrinogen degradation of greater than 30%. Surprisingly, the "maximum safety" achieved by the new methods described herein is defined as a fibrinogen degradation of less than 30%, which would not be associated with excess bleeding and would be clinically acceptable.

For example, the tPA-mproUK combination can lyse 50% of the mass of at least one blood clot, e.g., multiple blood clots, in less than an hour, e.g., 48, 50, 55, 60, 65, 70, 75, or 80 minutes. The combination also allows significantly lower doses to be used, which are far more fibrin-specific, safer, and more economical. mproUK, e.g., M5, is used instead of native pro-UK because mproUK is more stable in plasma at therapeutic doses and remains in its fibrin-specific pro-enzyme form, while native pro-UK tends to spontaneously convert into urokinase, which is a non-specific plasminogen activator that can cause bleeding complications. This is why pro-UK was denied market approval by the EMEA in Europe, following which its development also ceased in this country.

As shown in the examples below, when incubated in plasma in the absence of a blood clot, the very lose doses used in the tPA-mproUK combination do not induce any degradation of fibrinogen, and it is thus expected that the same combination will have little or no effect on coagulation or wound healing. In addition, since M5 is a proenzyme and requires fibrin for its activation, it is expected to be safe even in the presence of bleeding, e.g., during a hemorrhagic stroke. Furthermore, C1-inhibitor, which is available as a pharmacological agent, can be used to quench any non-specific activity of any mUK that may be formed during fibrinolysis (Pannell, J Thromb Haemost. 5(5):1047-54, 2007), e.g., in tests done in vitro as well as in therapy in vivo, if required. This C1-inhibitor effect is not shared by UK, and is unique to the proUK mutant.

Clinically, the tPA-mproUK combination therapy can be used to treat patients with stroke or heart attack symptoms without the delay caused by time-consuming diagnostic procedures, which are currently mandatory due to the significant bleeding risk associated with tPA in treating stroke. Treatment can be administered on suspicion or in the ambulance. Since time is of the essence for survival and clinical outcome of those patients, the combination therapy offers better efficacy and outcome than tPA as a monotherapy, which is the only therapy currently approved and available. The therapeutic benefit of tPA monotherapy in treating stroke remains controversial, and its authorization has been recently questioned (Sandercock P, Lancet. 2014 Aug. 23; 384(9944):660-1). The mproUK preferentially activates plasminogens in the "bad" occlusive clots while sparing plasminogens in the "good" wound-sealing clots. Therefore, there is little risk of opening up a hemostatic site. By contrast, tPA targets such site which are made up of intact fibrin, as described above in Step 1 of fibrinolysis. Free plasminogen in the plasma is also protected by the action of C1-inhibitor, so there is less risk of inducing a hemophilia-like state.

The maximum clot lysis rate of the present methods can be determined in vivo can be determined, for example, by standard techniques for assessing blood vessel recanalization. For example, the grade of blood vessel occlusion can be assessed in analogy to the Thrombolysis In Myocardial Infarction (TIMI) score, wherein a TIMI score of 0 is complete occlusion, TIMI of 1 is minimal perfusion, TIMI of 2 is partial flow (recanalization), and a TIMI score of 3 is complete flow. The TIMI study group developed this grading scale for coronary blood flow based on visual assessment of the rate of contrast opacification of the infarct artery (see, e.g., The TIMI Study Group. The Thrombolysis in Myocardial Infarction (TIMI) trial: phase I findings. N Engl J Med. 1984; 33:523-530; and The TIMI Study Group. Comparison of invasive and conservative strategies after treatment with intravenous tissue plasminogen activator in acute myocardial infarction: results of the Thrombolysis in Myocardial Infarction (TIMI) phase II trial. N Engl J Med. 1989; 320:618-627, which are incorporated herein by reference for their description of the TIMI grading scale).

The TIMI flow grade has become the standard for semi-quantitative evaluation of myocardial perfusion before and after coronary reperfusion therapies as well as for determining therapies for stroke. Both TIMI flow grades 2 and 3 have been considered indicative of successful reperfusion. Thus, as used herein, a maximum clot lysis rate is expected to be associated in human subjects or patients with achieving a TIMI score of 2 or better within about 75 minutes or less, e.g., within 70, 65, 60, 55, 50, 45, 40, 35, or 30 minutes.

Plasminogen Conformations and Distinction Between "Good" and "Bad" Blood Clots

Plasminogen can take on at least three different conformations before converting to active plasmin. The first conformation is the native "closed" conformation, i.e., unbound to any fibrin, and plasminogen exists in the blood in this first conformation. Urokinase can activate plasminogen in this first conformation and may cause non-specific hemorrhagic diathesis, i.e., a hemophilia-like state. Since pro-UK at therapeutic doses is unstable and readily converts to urokinase at therapeutic concentration, pro-UK can also cause hemophilia-like side-effects.

When bound to fibrin, plasminogen can adopt two or three different "open" conformations, providing a basis to distinguish the good wound-healing clots from bad occlusive clots. The first of these is the plasminogen conformation that takes place when plasminogen binds to an internal lysine in the D-domain of intact fibrin. The second of these is the plasminogen conformation that occurs when plasminogen binds to the three C-terminal lysines on fibrin fragment E, which is exposed only after some fibrin degradation as described above in Step 2 of fibrinolysis.

When hemostatic fibrin forms to seal an injury, it acts like a bandage and causes no interference with blood flow. The intact fibrin in such a hemostatic clot has only an internal plasminogen-binding site located in the D-domain, which induces the first of these fibrin-bound conformations. In this conformation, plasminogen is susceptible to activation by tPA, whose fibrin binding site is adjacent, but not by pro-UK, which does not bind to fibrin and has substrate binding due to the second conformation induced by the fibrin E-domain.

When a thrombus forms in a blood vessel, it impedes or arrests blood flow and triggers the local release of tPA from the occluded blood vessel wall and leads to fibrin degradation. Fibrin degradation exposes a new plasminogen-binding site on fibrin fragment E. Plasminogen binds to this new binding site on fibrin fragment E. Pro-UK preferentially activates plasminogen bound to fibrin fragment E.

Utilization of this important distinction between the "good" and the "bad" fibrin clots can effectively achieve thrombolysis while protecting hemostatic plugs that seal injuries. Pro-UK mutant has the same mode of action as pro-UK.

A third fibrin-bound plasminogen conformation exist when plasminogen binds to a single C-terminal site, believed to be on the fibrin gamma chain.

Tissue Plasminogen Activator

Tissue plasminogen activator is a serine protease stored in endothelial cells lining the blood vessel wall. When a thrombus occludes a blood vessel, tPA is released from the blood vessel wall and lyses fibrin clots.

Currently most therapeutic thrombolysis is performed using tissue plasminogen activator (tPA) and its derivatives, however, tPA can cause hemorrhagic side effects. For example, tissue plasminogen activator (tPA) at a dose of 150 mg has been shown to induce superior coronary thrombolysis, but has been accompanied by an unacceptable incidence of intracranial hemorrhage, obliging the adoption of a less effective dose of 100 mg (Braunwald, J Amer Coll Cardiol. 9: 467, 1987; Grossbard, J Amer Coll Cardiol. 9:467, 1987). In comparative clinical trials in acute myocardial infarction (AMI) patients, results with percutaneous coronary intervention (PCI) were significantly better than intravenous administration of tPA, although PCI is more costly, technically demanding, and time-consuming. This clinical outcome was surprising, but can be explained by the following tPA properties: (1) the therapeutic dose of tPA is limited by the intracranial hemorrhage complications; and (2) tPA's efficacy is undermined by a relatively high coronary rethrombosis rate, which is associated with hematological evidence of thrombin generation (Verheugt, J Am Coll Cardiol 1996, 27: 766-773; Gurewich, Circulation 1993, 87: 1759-1761; Rapold, Blood 1991, 78: 1490-1495; Gulba, Lancet 1988, 2: 97; Gulba, Circulation 1991, 83: 937-944).

In ischemic stroke, a further dose reduction was required due to a 20% incidence of intracranial hemorrhage complications when administering tPA at doses equivalent to those used in AMI (Hacke, JAMA 1995, 274: 1017-1025). The use of heparin, which is used with tPA in AMI, is precluded in stroke, as reocclusion rates of 14-31% have been reported (Alexandrov, Neurology 2002, 59: 862-867; Rubiera, Stroke 2005, 36: 1452-1456; Saqqur, Stroke 2007; 38: 69-74). The net result has been that only about 2-5% of patients with ischemic stroke are treated with tPA in the United States (Kleindorfer, Stroke 2008; 39: 924-928).

tPA-induced bleeding is believed to be primarily related to lysis of hemostatic fibrin needed to repair injury sites in the vessel wall, which are usually occult and unpredictable, but tPA dose-dependent. proUK/M5 spares these sites due its different mode of action, as described above.

Pro-Urokinase and Pro-Urokinase Mutants

Pro-urokinase (pro-UK)(SEQ ID NO:1) is less well-known as a thrombolytic drug, but Phase 3 clinical studies in acute myocardial infarction have been completed (Michels R, J Thromb Thrombolysis 1995, 2: 117-124; PR1MI Trial Study Group. Lancet 1989, 1: 863-867; Tebbe U, J Am Coll Cardiol 1998, 31: 487-493). Pro-UK induced little (5%) or no coronary rethrombosis and no hematological evidence of thrombin generation in these studies (PRIMI Trial Study Group. Lancet 1989, 1: 863-867; Weaver, J Am Coll Cardiol 1994, 241: 242-1248). Unfortunately, at therapeutic doses, pro-UK became vulnerable to spontaneous activation into the enzyme form, two-chain urokinase (tcUK), in plasma. When this occurred, it incurs a bleeding risk, and for this reason, marketing approval was denied and pro-UK development was abandoned in the West.

The instability of pro-UK was related to its relatively high intrinsic catalytic activity. Structure-function studies revealed the charged residues in a flexible loop consisting of amino acid residues 297-313 in the catalytic domain are responsible for this activity. Mutagenesis in the flexible loop region resulted in modulation of the intrinsic activity of pro-UK (SEQ ID NO:1). Exemplary pro-UK "flexible loop" mutants with reduced intrinsic catalytic activity are described in U.S. Pat. No. 5,472,692 (incorporated herein by reference in its entirety), such as Gly299→Ala mutant, Lys300→His mutant (known as "M5" or "M5 mutant"), Lys300→Ala mutant, and Glu301→His mutant.

The instability of pro-UK was related to its relatively high intrinsic catalytic activity. Structure-function studies revealed the charged residues in a flexible loop consisting of amino acid residues 297-313 in the catalytic domain are responsible for this activity. Mutagenesis in the flexible loop region resulted in modulation of the intrinsic activity of pro-UK. Exemplary pro-UK "flexible loop" mutants with reduced intrinsic catalytic activity are described in U.S. Pat. No. 5,472,692 (incorporated herein by reference in its entirety), such as Gly299→Ala mutant, Lys300→His mutant (known as "M5" or "M5 mutant"), Lys300→Ala mutant, and Glu301→His mutant.

One of these pro-UK "flexible loop" mutants, M5 (Lys300→His), has been tested both in vitro and in vivo, and was shown to dissolve blood clots much faster than native pro-UK (Liu et al., Circulation Research, 90:757-763, 2002). The intrinsic activity of the single-chain M5 mutant is five-fold lower than pro-UK, so M5 is more stable in blood than native pro-UK and less likely to spontaneously convert into active enzyme form and cause hemophilia-like side effects (Liu, Biochemistry 1996, 35: 14070-14076). The activity of the two-chain enzymatic form of mproUKs, e.g., M5, and the mode of action of mproUKs, e.g., M5, remain the same as native pro-UK (Sun Z, J Biol Chem 1997, 272: 23818-23823; Liu, Circu. Res. 2002, 90: 757-763). mproUKs like M5 possess another superior property; they can be inhibited by endogenous plasma C1-inhibitor, providing protection against non-specific side effects without interfering with fibrinolysis by mproUK (Gurewich, J Thrombos Haemost, 2006, 4: 1559-1565; Pannell, J Thromb Haemost, 2007, 5: 1047-1054; Gurewich, Thromb Haemost, 2009, 102: 279-286). Importantly, mproUKs such as M5 do not show any hemorrhagic side effects normally associated with thrombolytic agents as described in U.S. Pat. No. 7,074,401 (incorporated herein by reference in its entirety). In addition, mproUKs such as M5 can be synthesized according to the methods described in U.S. Pat. No. 7,070,958 (incorporated herein by reference in its entirety).

M5 and other mproUKs are expected to be safe for human administration, because (1) they are essentially a natural human protein (99.8% similarity to native pro-UK), (2) they are free of antigenic (immunologic) reactions, and (3) naturally occurring human pro-UK and recombinant human pro-UK from *E. coli* have already been safely administered to about 5,000 human patients in Phase III clinical studies.

Combination Therapy of Low Dose tPA and mproUK

By utilizing the complementary mechanism of action of tPA and pro-UK on plasminogen action, the present inventor has demonstrated that fibrinolysis at a maximum clot lysis rate can be attained with a combination of a mini-dose of tPA (at 2-5% of the standard 100 mg dose, e.g., 1.0, 2.0, 2.5, 3.0, 3.5, 4.0, or 4.5 mg bolus) plus an infusion of mproUK, e.g., M5, (at 40-50% of monotherapy dose, e.g., 60 to 120 ug/ml infused over 60-90 minutes) giving a maximum clot lysis rate, which is at least as fast as the maximum clot lysis rate that can be achieved by monotherapy with either tPA or mproUK alone at their maximal effective dose (FIGS. 1A to 5B). For example, the tPA-mproUK combination can lyse 50% of the mass of blood clots in less than an hour, e.g., 48 minutes, on average (see FIG. 7, tPa+MF). Although tPA and mproUK (M5) alone can achieve similar lysis time at very high doses, e.g., tPA at 3 µg/ml or mproUK (M5) at 15 µg/ml (FIG. 7), non-specific activation of plasminogen and resultant fibrinogen degradation of about 77% for M5 (see FIG. 2B) and about 80% for tPA (see FIG. 1B) can occur at those doses and cause significant and clinically unacceptable hemophiliac-like side effects.

mproUK such as M5 is used instead of native pro-UK, because mproUK is more stable in plasma and remains in proenzyme form while native pro-UK tends to spontaneously convert into urokinase and cause hemophiliac-like side effects. Thus, the maximum clot lysis rate can be achieved by the tPA-mproUK combination with only a fraction of the monotherapy doses of tPA and mproUK.

When incubated in plasma in the absence of a blood clot, the tPA-mproUK combination does not induce any degradation of fibrinogen (FIG. 9), and thus is expected to have no effect on coagulation and wound healing in vivo. Furthermore, C1-inhibitor can be used to quench any non-specific activity of mUK (the enzymatic form of mproUK) in plasma (FIGS. 2D and 6), adding further protection against bleeding complications.

Clinically, the tPA-mproUK combination therapy can be used to treat patients with stroke or heart attack symptoms without the delay caused by time-consuming diagnostic procedures. Provided herein are methods of treating a subject with symptoms of stroke or acute myocardial infarction by (a) identifying a subject who potentially had a stroke or acute myocardial infarction by observing one or more symptoms without determining the underlying cause of the stroke or acute myocardial infarction; and (b) administering to the subject a bolus of a first composition comprising 5 mg or less of tPA followed by an infusion of a second composition of mproUK at a rate of 60 to 120 mg/hour infused over 60 to 90 minutes. The second composition can be administered about 5, 10, or 15 minutes after the administration of the first composition. The first composition and the second composition are administered in an amount to lyse any blood clot that causes the symptoms of stroke or acute myocardial infarction at a maximum lysis rate. The first composition can include 2 to 5 mg of tPA, e.g., about 2 mg, about 2.5 mg, about 3 mg, about 3.5 mg, about 4 mg, about 4.5 mg, about 5 mg. The second composition that includes an mproUK like M5 can be administered by intravenous infusion. The intravenous infusion of mproUK like M5 can be performed at a dose of about 60-120 mg/hour (e.g., 60-100, 70-90, or 75-85 mg/hour) for 60, 70, 80, or 90 minutes.

The methods described herein can be used to treat stroke. A stroke can be ischemic or hemorrhagic. Ischemic stroke is caused by a thrombus obstructing blood flow, while hemorrhagic stroke is caused by a broken blood vessel. About 85% of the time, a stroke is ischemic, e.g., caused by a blood clot, and is therefore amenable to treatment by a thrombolytic agent. The timing of reperfusion after an ischemic stroke is critical, because the longer the brain cells are without oxygenated blood, the more brain cells are lost. However, it is difficult and time consuming to fully diagnose the cause of a stroke, yet an accurate diagnosis is critical for treatment with currently available thrombolytic agents due to the high risk of hemorrhagic side effects. Administering a thrombolytic agent to an ischemic stroke patient may be a proper therapy, but administering the same thrombolytic agent to a hemorrhagic stroke patient will exacerbate the problem and can kill the patient. Although it takes time to confirm a diagnosis, the basic symptoms of stroke exhibited by a person (such as sudden onset of one-sided paralysis) can be readily determined by one skilled in the medical field, such as an EMT, a nurse, or a doctor, or even a layperson with minimal training.

A subject with symptoms of stroke can be treated using the methods described herein by administration of a bolus of a low dose of tPA followed by an infusion of mproUK. The very low dose of tPA in the combination reduces potential hemorrhagic risk. Since the tPA in the combination is a mini-dose and the mproUK can lyse a thrombus but spare hemostatic fibrin, the combination can be used to treat patients with a possible ischemic stroke safely with little risk of aggravating bleeding in the brain. Thus, it is possible to initiate treatment in the ambulance on the basis of a clinical suspicion of the diagnosis.

The methods described herein can also be used to treat heart attack, e.g., acute myocardial infarction. A heart attack occurs when one of the coronary arteries is blocked, e.g., by a blood clot. The timing of reperfusion after a heart attack is critical, because the longer the heart muscle is without oxygenated blood, the more muscle cells are damaged or lost. The present treatment of choice is by catheterization and angioplasty, which requires hospitalization, an available catheterization room and staff at the ready. This delays treatment and carries a high cost. This first one hour after a coronary occlusion has been called the "Golden Hour," because it is the time during which the maximum salvage of heart muscle and the maximum reduction in mortality is possible. Pretreatment with tPA to gain time before catheterization has been generally abandoned since multiple studies have shown that tPA significantly increase the complication rate with catheterization.

A subject with symptoms of a heart attack can be treated by administration of a bolus of a low dose of tPA followed by an infusion of an mproUK such as M5 as described herein. Experience has shown that pretreatment with pro-UK is not associated with post catheterization complication, so that pretreatment with the combination should be well tolerated and may also reduce the need for the subsequent catheterization.

C1-Inhibitor

C1-inhibitor is a 104 KD serine protease inhibitor with a normal plasma concentration of about 250 μg/ml and a half-life of about 28 hours. Deficiency of this protein has been associated with a disease called hereditary angioedema. C1-inhibitor has long been administered clinically for the treatment of hereditary angioedema. Commercially available C1-inhibitors include CINRYZE®, CETOR®, BERINERT®, and RUCONEST®.

The active enzymes two-chain UK or mUK generated during fibrinolysis are eventually released into the plasma where plasminogen activation becomes a liability. Quenching this activity requires plasma inhibitors. As described in U.S. Pat. No. 7,837,992 (incorporated herein by reference), an inhibitor complex of C1-inhibitor appeared within minutes of the incubation of enzyme mUK with human or dog plasma. C1-inhibitor is present endogenously in human body and can be supplemented pharmacologically. The endogenous C1-inhibitor was shown to be very effective in quenching activity of mUK, e.g., tcM5, but not UK activity (Gurewich V, J Thrombos Haemost, 2006; 4: 1559-1565; Pannell R, J Thromb Haemost, 2007; 5: 1047-1054; Gurewich, Thromb Haemost, 2009; 102: 279-286). As shown in U.S. Pat. No. 7,837,992, the C1-inhibitor by inhibiting mUK effectively stabilized the mproUK like M5 in plasma and allowed a higher concentration of mproUK like M5 to be tolerated without compromising fibrin-specificity.

The methods of treating a subject with symptoms of stroke or acute myocardial infarction disclosed herein can further include administration of a third composition comprising a C1-inhibitor to the subject. The C1-inhibitor can be administered as a bolus in an amount sufficient to establish a concentration of C1-inhibitor in the subject's plasma that is within the range of two to three times above normal physiological level of C1-inhibitor (about 250 μg/ml), i.e., about 500-750 μg/ml. For example, the third composition can include 500-1500 mg of C1-inhibitor. In some embodiments, the third composition can be administered to the subject before the administration of the second composition. In some embodiments, the third composition can be administered to the subject simultaneously with the second composition.

Pharmaceutical Compositions, Dosage Regimens, and Methods of Administration

Pharmaceutical compositions provided herein can include specific dosages of tPA and a pro-UK mutant such as M5 as active ingredients. The active ingredient of a pharmaceutical composition, e.g., tPA or mproUK, can be formulated for delivery by intravenous injections.

Methods of formulating suitable pharmaceutical compositions are known in the art, see, e.g., Remington: The Science and Practice of Pharmacy, 21st ed., 2005; and the books in the series Drugs and the Pharmaceutical Sciences: a Series of Textbooks and Monographs (Dekker, N.Y.). For example, solutions or suspensions used for parenteral administration can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid EDTA); buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injection can include sterile aqueous solutions (where water soluble), dispersions, and sterile powders for the extemporaneous preparation of sterile injectable solutions or dispersion. For intravenous administration, suitable carriers include physiological saline, bacteriostatic water, Cremophor EL™ (BASF, Parsippany, N.J.), or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants.

Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

The pharmaceutical compositions can be included in a container, pack, or dispenser together with instructions for administration.

Dosage regimens can be adjusted to provide the optimum therapeutic response. See e.g., Physicians' Desk Reference, 63rd edition, Thomson Reuters, Nov. 30, 2008. For example, Dosage, toxicity and therapeutic efficacy of the therapeutic compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The tPA bolus can include 2-5 mg of tPA, e.g., about 2 mg, about 2.5 mg, about 3 mg, about 3.5 mg, about 4 mg, about 4.5 mg, or about 5 mg. The intravenous dose of mproUK, e.g., M5, can be 60-120 mg/hour (e.g., 60-100, 70-90, or 75-85 mg/hour) for 60, 65, 70, 75, 80, 85, or 90 minutes. The C1-inhibitor can be administered as a bolus in an amount sufficient to establish a concentration of C1-inhibitor in the subject's plasma that is about 500-750 µg/ml. For example, the C1-inhibitor bolus can include 500-1500 mg of C1-inhibitor.

For patients with stroke or acute myocardial infarction, the time needed to reperfusion is critical to survival and clinical outcome. These findings suggest that a combination of mini-dose tPA and M5 can achieve therapeutic thrombolysis in a safer and more effective way. Thus, patients with stroke or acute myocardial infarction can be treated with a combination of tPA and M5 with little or no delay.

Efficacy of thrombolysis is defined by the rate of lysis. However, the clinical utility requires that efficacy be divided by the incidence of bleeding complications from that rate. With the combination therapy described herein, the evidence is that there is no maximum clinical utility, since the optimum combination induces a maximum rate of lysis without significant fibrinogen degradation (see Pannell et al., PLOS ONE, DOI:10.1371/journal.pone.0122018 Mar. 26, 2015, which is incorporated herein by reference in its entirety). This makes for a far superior clinical utility index, in fact it gives the maximum utility index possible, i.e., the maximum clot lysis rate possible for plasminogen activators without side effects.

Kits

Also provided herein are kits that include at least a composition comprising tissue plasminogen activator (tPA) in one container and another composition comprising an mproUK, e.g., M5, in a separate container. The kits are used to carry out the therapeutic methods described herein. The first composition can be formulated suitable for administration as a bolus, and can include 2-5 mg of tPA. The second composition can be formulated suitable for intravenous infusion. The second composition can include 60-120 mg (e.g., 60, 65, 70, 75, 80, 85, or 90 mg) of the pro-UK mutant, for infusion over a time period of 60-90 minutes. The kit can also include a third composition comprising C1-inhibitor. The third composition can be formulated suitable for administration as a bolus, and can include about 500-1500 mg of C1-inhibitor.

Kits generally include the following major elements: packaging, reagents comprising binding compositions as described above, optionally a control, and instructions. Packaging can be a box-like structure for holding a vial (or number of vials) containing the compositions, and instructions for use in a method described herein. Individuals skilled in the art can readily modify the packaging to suit individual needs.

Compositions and kits provided herein can be used in accordance with any of the methods (e.g., treatment methods) described above. For example, compositions and kits containing a composition comprising tPA and another composition comprising a pro-UK mutant, e.g., the M5 mutant, can be used to treat stroke, heart attack, or other cardiovascular diseases caused by a thrombus such as peripheral gangrene. Those skilled in the art will be aware of other suitable uses for compositions and kits provided herein, and will be able to employ the compositions and kits for such uses.

EXAMPLES

The invention is further described in the following examples, which do not limit the scope of the invention described in the claims.

Example 1. Maximum Clot Lysis Rate Thrombolysis In Vitro by tPA/M5

The fibrinolytic and fibrinogenolytic effects of specific combinations of tPA and M5 were studied in vitro in a human plasma milieu.

Materials

The mproUK that comprises a substitution of histidine for lysine at amino acid position 300 (Lys300→His) of pro-urokinase (M5) was prepared from *E. coli* by PxTherapeutics (Grenoble, France). Tissue plasminogen activator (tPA) was obtained from Genentech (South San Francisco, Calif.). Human Fibrinogen, Kabi Grade L, was obtained from Chromogenix, Milan, Italy. Aprotinin and fluorescein isothiocyanate were from Sigma Chemicals, St. Louis, Mo. Thrombin (ThromboMax, 100 NIH U per ml) was obtained from Sigma (St Louis, Mo.). Clinical grade C1-inhibitor was obtained from CSL Behring, Marburg, Germany. Human outdated blood bank plasma, pooled from four donors, was used in the experiments.

Note that various animal models have different sensitivities to human pro-UK (see, e.g., Table 1 in Gurewich et al., J. Clin. Invest., 73:1731-1739 (1984), which is incorporated herein by reference in its entirety. Thus, animal dosages cannot be used to determine human dosages, and the dosages described here are based on experience using the individual components in human tests. In vitro studies in human plasma show that 2× as much M5 is needed than proUK for the same lysis rate. The monotherapy dose of proUK/M5 is known from Phase-3 studies and the newly discovered mini-dose tPA plus the low dose of M5 in the combination therapy methods described herein are based on this 2× factor.

Blood Clot Lysis Experiments

Fibrinolysis by M5 was studied in an inhibitor-containing plasma milieu. Blood clots were made by recalcification of 0.2 ml pooled blood bank plasma with 35 mM of calcium in the presence of a trace amount of thromboplastin and a fluoresceinated fibrinogen (see Dmitry V, J Biol Chem, 1996; 271: 2133-2138). The blood clots were then incubated for an hour at 37° C., followed by overnight incubation at room temperature. The following day, the blood clots were placed into 2 ml of blood bank plasma, followed by addition of tPA, M5, or the combination of tPA and M5. Clot lysis was monitored by taking 50 μl samples of the plasma at certain time points and measuring fluorescence emission. The fluorescence emission in the sample represents the amount of fibrin degradation products released from the blood clots. In some experiments, the volume of plasma was increased to 5 ml, and unlabeled fibrinogen was added to make up for the dilution of fluoresceinated fibrinogen. In those experiments, the end of blood clot lysis was determined visually.

Each blood clot lysis experiment was performed in triplicate. Graph Pad Prism was used to prepare graphs and conduct statistical analysis.

The lysis curves were plotted as a percentage lysis of blood clots over time. The 100% point was obtained from the mean of the highest readings. The base line reading was obtained at onset by subtracting the amount of fluorescence shown by the plasma (~15% of the full signal) to obtain the zero point. The time to 50% lysis for each experimental condition was determined from the lysis graph and was used as the principal endpoint.

Determination of Remaining Fibrinogen after Blood Clot Lysis

After blood clot lysis was completed, a final plasma sample (1.0 ml) was obtained for determining the remaining fibrinogen. Aprotinin (200 KIU/ml) was added to the sample to prevent further proteolysis. The remaining fibrinogen was recorded as the percentage of the baseline (BL) fibrinogen.

Fibrinogen was measured as a thrombin-clottable protein. After dilution of the plasma sample with an equal amount of phosphate-buffered saline, 200 μl of thrombin (1,000 NIH units/ml solution) was added. The solution was mixed gently, and incubated for an hour at 37° C., followed by overnight incubation at room temperature. The following morning, each blood clot was wound onto a thin, long stemmed plastic transfer pipette tip, to which the gel adhered, and the serum content expressed by pressure against the test tube wall and then against a paper towel. The white fibrin on the pipette stem was then placed in at least 5 ml of saline for at least an hour to allow diffusion of any remaining serum proteins. The fibrin was then peeled off the tip and placed into 1 ml of 5% NaOH, boiled for one minute, and then kept at room temperature until all fibrin had gone into solution. The protein in the solution was measured spectrophotometrically at 280 nm.

Determination of the Shortest Time to Lysis by tPA or M5 Alone

The blood clot lysis experiments were performed as described above in the presence of 1, 2, or 3 μg/ml of tPA. The lysis curves were plotted as a percentage lysis of blood clots over time, and the time used to lyse 50% blood clots for each experimental condition was determined from the lysis curve. The shortest time to lysis (from which the maximum clot lysis rate can be determined) was defined as the time at which there is no further dose-dependent shortening of the lysis time. The results of a representative experiment are shown in FIG. 1A and the shortest time used to lyse 50% blood clots by tPA, was found to be 60 minutes when 3 μg/ml of tPA was used. Thus, the maximum clot lysis rate is 50% lysis at one hour.

Figure 1B:
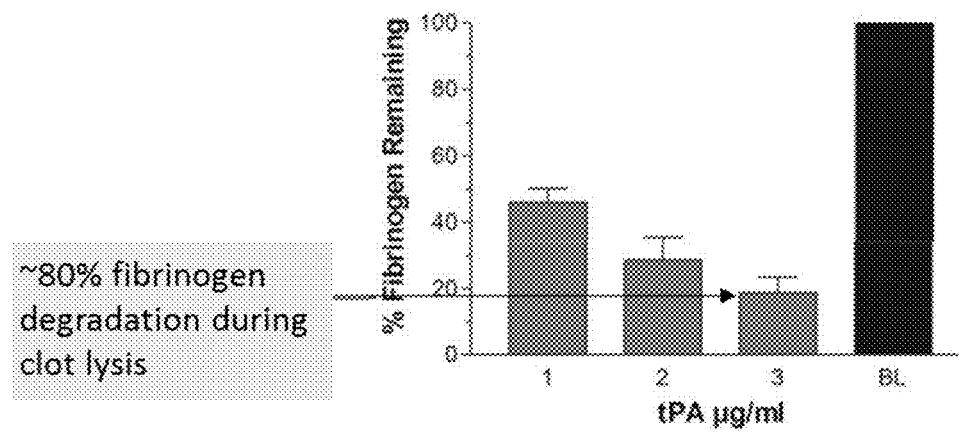
FIG. 1B is a bar graph showing remaining fibrinogen at the end of clot lysis, expressed as percentage of the baseline (BL).

FIG. 1B shows the percentage of the remaining fibrinogen of the baseline level at the end of lysis for each tPA dose tested, ranging from 19% to 45%. Thus, tPA alone caused 55%-81% fibrinogen degradation.

Figure 2A:
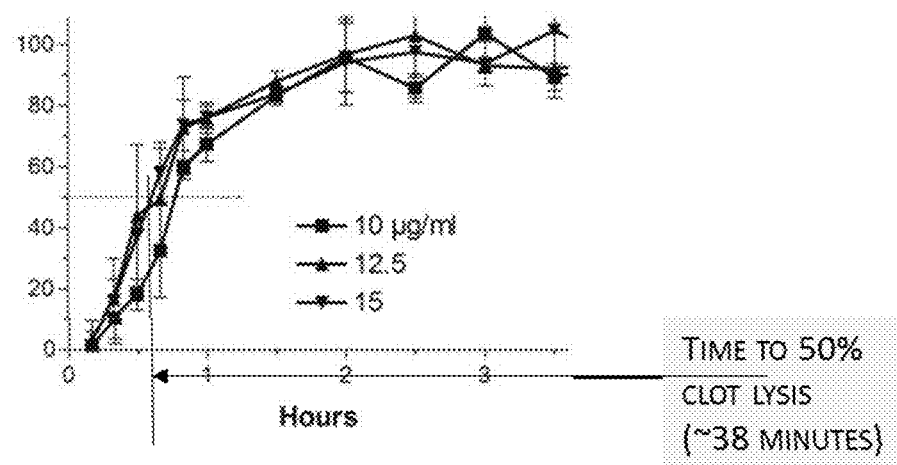
FIG. 2A is a line graph showing the lysis of fluorescein-labeled plasma clots by mproUK (M5) at three doses: 10, 12.5, or 15 µg/ml. The time used by M5 to lyse 50% of the plasma clots at a saturated dose of 15 µg/ml is 50 minutes.

For M5, the blood clot lysis experiments were performed as described above in the presence of 10, 12.5, 15 μg/ml of M5. The shortest time used to lyse 50% blood clots by M5, was determined to be 50 minutes, when 15 μg/ml of mproUK was used (FIG. 2A). Thus, the maximum clot lysis rate is 50% clot lysis at 50 minutes.

Figure 2B:
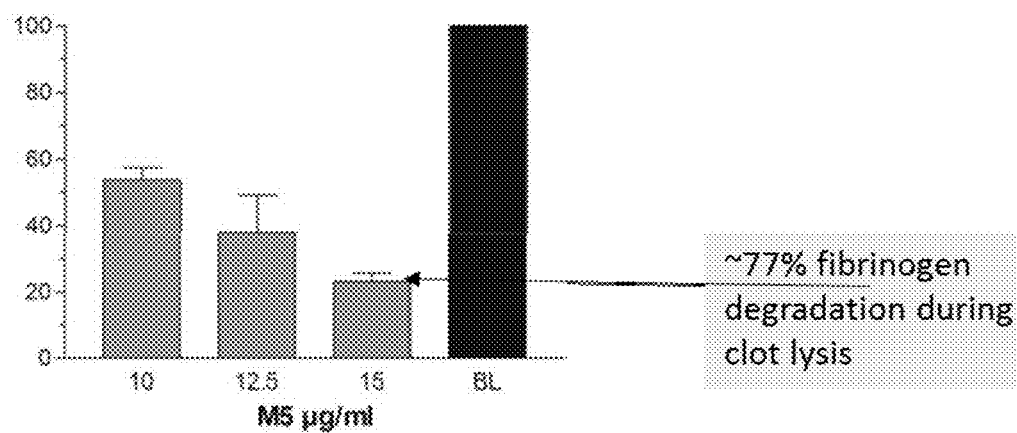
FIG. 2B is a bar graph showing remaining fibrinogen at the end of clot lysis, expressed as percentage of the baseline (BL).

The percentage of the remaining fibrinogen of the baseline level at the end of lysis for each M5 dose, ranging from 25% to 55%, is shown in FIG. 2B. Thus, M5 alone caused 45%-75% fibrinogen degradation.

Effect of C1-Inhibitor on Fibrinogenolysis by M5

Figure 2C:
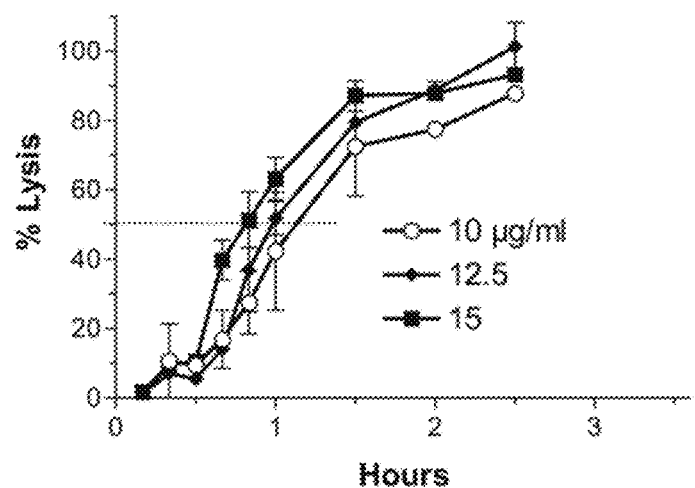
FIG. 2C is a line graph showing the time used by mproUK (M5) to lyse fluorescein-labeled plasma clots was unaffected by the Cl-inhibitor (750 µg/ml).
Figure 2D:
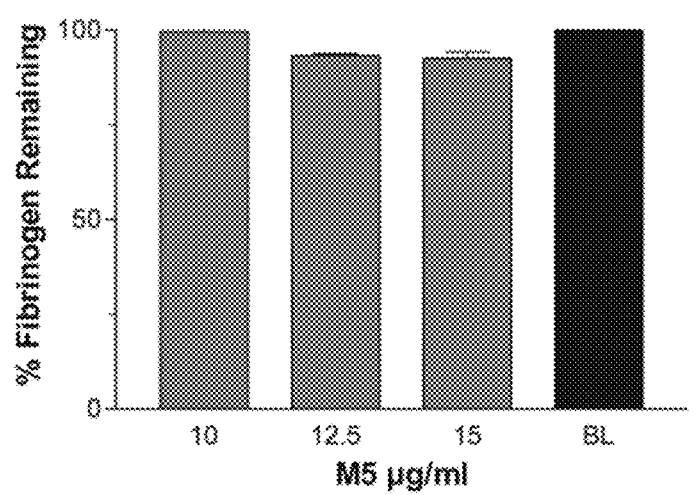
FIG. 2D is a bar graph showing fibrinogenolysis by M5 was prevented by the Cl-inhibitor (750 µg/ml).

To prevent fibrinogenolysis, 750 μg/ml of C1-inhibitor was added to the plasma prior to the addition of 10, 12.5, 15 μg/ml of M5 in the clot lysis experiments. The presence of 750 μg/ml of C1-inhibitor does not affect the time used to lyse 50% blood clots by M5, which was still 50 minutes (FIG. 2C). However, as shown in FIG. 2D, little fibrinogen degradation occurred in the presence of C1-inhibitor.

The C1-inhibitor experiment was not repeated for tPA, since C1-inhibitor has already been shown to inhibit blood blot lysis by tPA (Tomasi S, PLos One., 2011; 6: e21999).

Maximum Clot Lysis Rate by a Combination of Mini-Dose tPA and Low Dose M5

Figure 3:
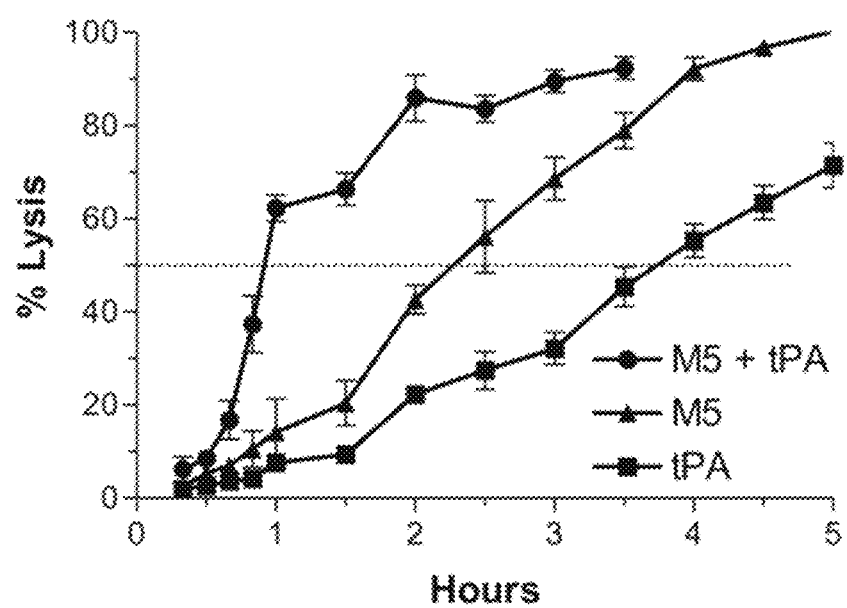
FIG. 3 is a line graph showing maximum clot lysis rate by a combination of tPA (0.2 µg/ml) and M5 (6 µg/ml) (circle). The combination induced clot lysis much faster than 0.2 µg/ml tPA (square) or 6 µg/ml M5 (triangle) alone. Results are representative of a single experiment performed in triplicate.

To determine the lowest dose of tPA and M5 that is needed to achieve the shortest lysis time (and maximum clot lysis rate) when used in combination, the blood clot lysis experiments were performed using various combinations and ratios of tPA and M5. The lowest doses of tPA and mproUK when used in combination to consistently achieve the maximum clot lysis rate were determined to be 0.2 μg/ml of tPA and 6 μg/ml of M5. These doses corresponded to 6% of the tPA dose required to achieve the shortest lysis time plus 40% of the M5 dose needed to achieve that when they were used alone in monotherapy. FIG. 3 shows the results of a representative clot lysis experiment, where the time used to lyse 50% blood clots by a combination of 0.2 μg/ml tPA and 6 μg/ml M5 was 53 minutes, whereas the time used to lyse 50% blood clots by 6 μg/ml M5 alone was 135 minutes and the time used to lyse 50% blood clots by 0.2 μg/ml tPA alone was 225 minutes. These results demonstrate that a small dose of tPA, e.g., 0.2 μg/ml, greatly shortened the clot lysis time by M5. This observation is consistent with tPA's function in initiating fibrinolysis.

Figure 4A:
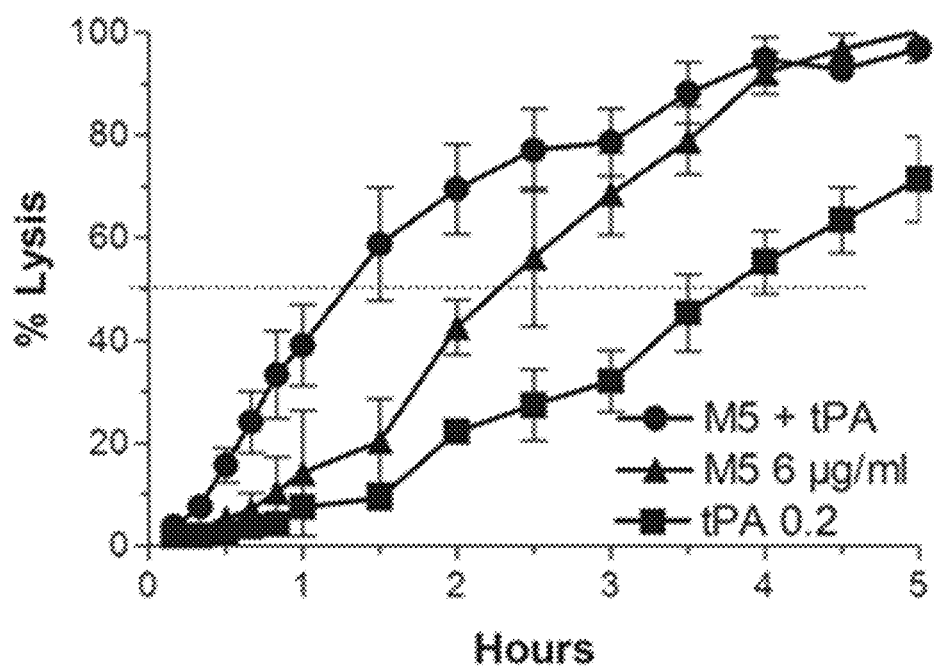
FIG. 4A is a line graph showing clot lysis by a combination of tPA (0.2 µg/ml) and M5 (6 µg/ml) (circle). The combination induced clot lysis much faster than 0.2 µg/ml tPA (square) or 6 µg/ml M5 (triangle) alone.
Figure 4B:
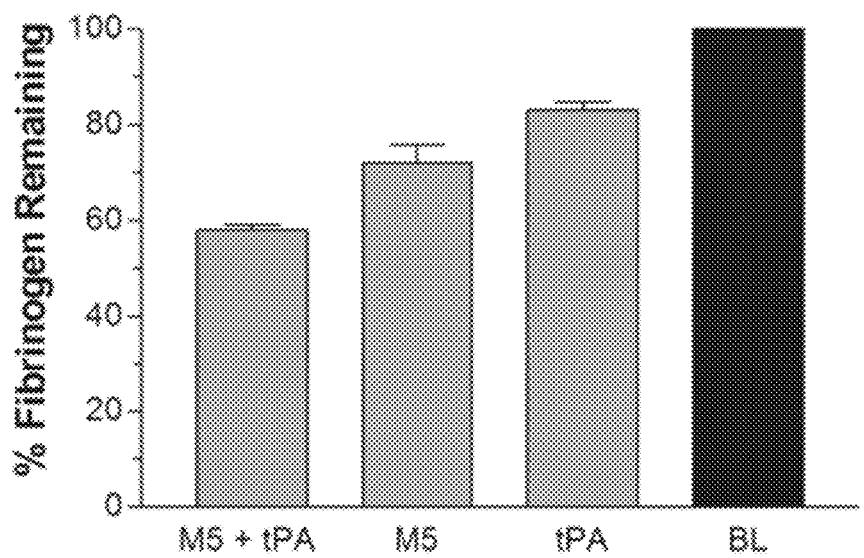
FIG. 4B is a bar graph showing the remaining plasma fibrinogen at the end of clot lysis, expressed as percentage of baseline (BL) fibrinogen. Results are representative of 10 experiments performed in triplicate.

The results of ten representative clot lysis experiments are shown in FIG. 4A, using the combination (0.2 μg/ml tPA+6 μg/ml M5) (circle), which induced an average 50% lysis time of approximately 75 minutes. At this dose of M5 alone (triangle), the lysis time was 135 minutes, and tPA alone (square) induced a lysis time of 225 minutes. The findings show that a mini-dose tPA caused about a 45% shortening of the onset of lysis by M5. FIG. 4B shows the plasma fibrinogens at the end of lysis, expressed as percentage baseline (BL) fibrinogen. All experiments were performed in triplicate.

Figure 6:
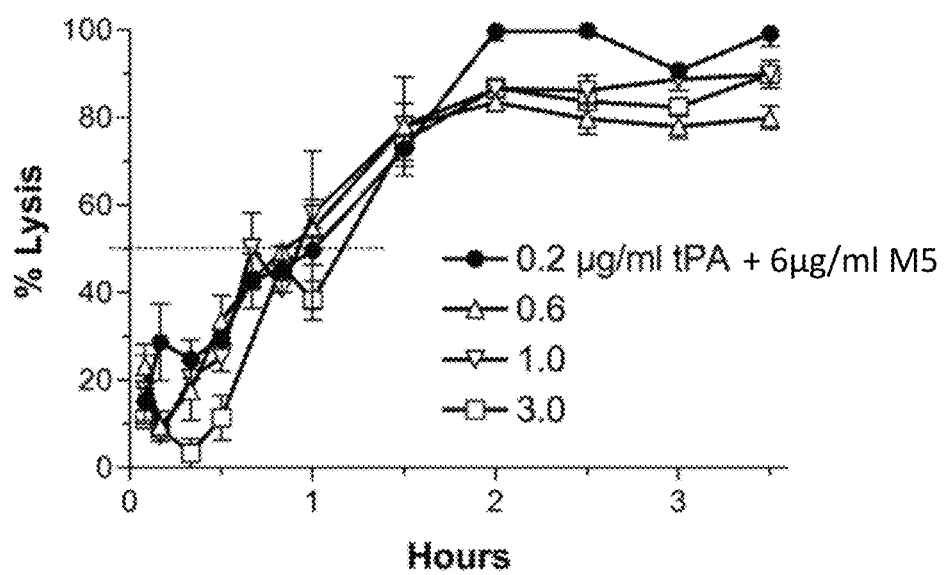
FIG. 6 is a line graph showing tPA doses higher than 0.2 µg/ml do not further enhance clot lysis rate when combined with 6 µg/ml M5.

To test if tPA's function in the combination is limited to the initiation of fibrinolysis, blood clot lysis experiments were performed using four tPA-M5 combinations. Each tPA-M5 combination includes a fixed dose of 6 µg/ml of M5 and a different tPA dose selected from 0.2, 0.6, 1.0, and 3.0 µg/ml. The time used to lyse 50% blood clots is about 48-60 minutes for all four combinations tested and a tPA dose higher than 0.2 µg/ml does not further shorten the time needed to lyse 50% blood clots (FIG. 6). These findings are consistent with tPA's function in the combination being essential for the initiation of fibrinolysis but not contribute to fibrinolysis beyond the initiation.

Figure 7:
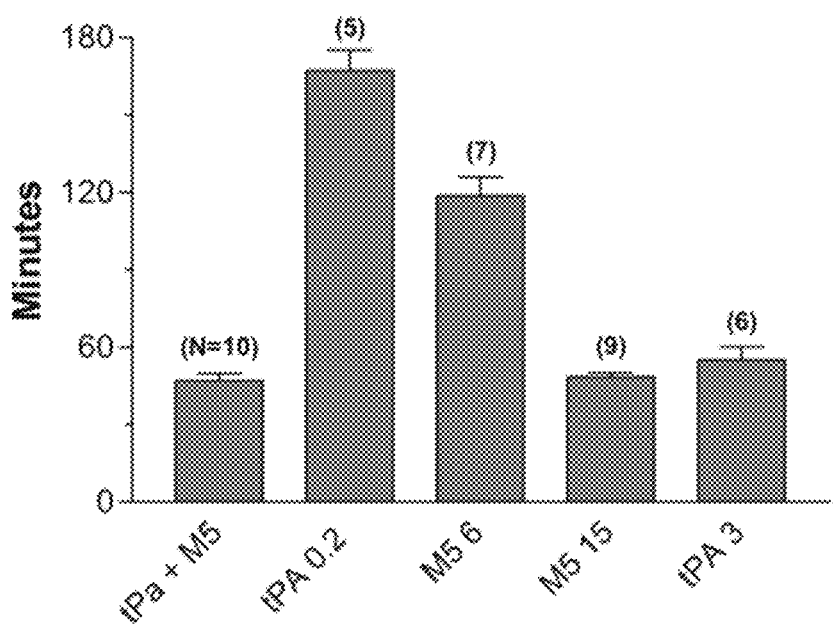
FIG. 7 is a bar graph showing the average time required to lyse 50% of the plasma clots by the combination of 0.2 µg/ml tPA and 6 µg/ml M5 ("tPA+M5"), 0.2 µg/ml tPA ("tPA 0.2"), 6 µg/ml M5 ("M5 6"), 15 µg/ml M5 ("M5 15"), 3 µg/ml tPA ("tPA 3"). Data are pooled from multiple experiments (the number of experiments is shown above each bar).

The average time used to lyse 50% blood clots in vitro, from multiple blood clot experiments were tabulated and compared. FIG. 7 shows that the mean time used to lyse 50% blood clots by the combination of 0.2 µg/ml tPA plus 6 µg/ml M5 was 48 (±2.5) minutes (n=10); the time used to lyse 50% blood clots by 0.2 µg/ml tPA alone was 156 (±5.3) minutes (n=5); for 6 µg/ml of M5 alone, it was 118 (±7.2) minutes (n=7); for 15 µg/ml of M5 alone, it was 48 (±1.6) minutes (n=9); and for 3 µg/ml of tPA alone, it was 55 (±5) minutes (n=6). The time used to lyse 50% blood clots by a combination of 0.2 µg/ml tPA plus 6 µg/ml M5 is significantly less than monotherapy of 0.2 µg/ml tPA alone or 6 µg/ml M5 alone (FIG. 7). Although tPA and mproUK alone can achieve similar clot lysis time at very high doses, e.g., tPA at 3 µg/ml or M5 at 15 µg/ml (FIG. 7), non-specific activation of plasminogen can occur at those doses and cause hemophiliac-like side effects.

Figure 8:
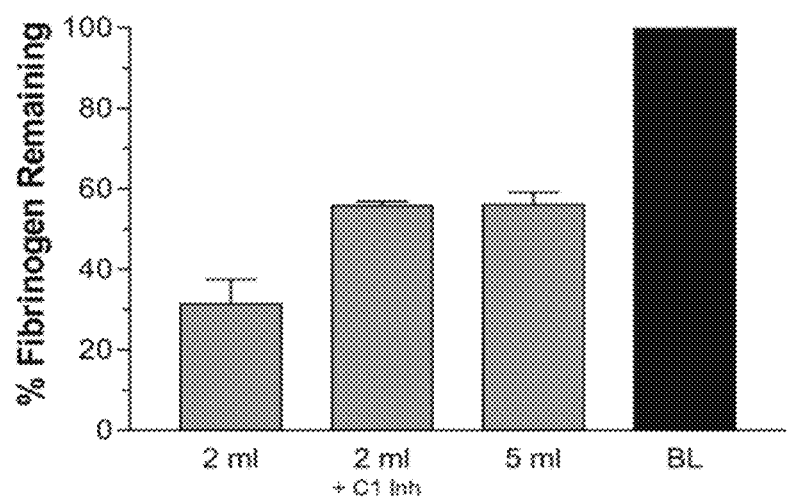
FIG. 8 is a bar graph showing the remaining fibrinogen (% BL) at the end of clot lysis by a combination of 0.2 µg/ml tPA and 6 µg/ml M5 under the different conditions tested, namely, (1) in 2 ml plasma; (2) in 2 ml plasma plus C1-inhibitor (500 µg/ml); and (3) in 5 ml plasma. Increases in plasma volume naturally decrease fibrinogen degradation (plasma volumes in human subjects are about 3000 ml on average) and thus the use of a C1-inhibitor is not likely required in vivo, but is useful in in vitro studies to better mimic in vivo conditions.

Effect of Volume and C1-Inhibitor on Fibrinogenolysis by the tPA and M5 Combination During fibrinolysis, mproUK is activated by plasmin and converted to mUK, which can then diffuse into the plasma. Confining proteolysis to the clot becomes a function of plasma inhibitors, e.g., C1-inhibitor. In a test tube, the limited plasma volume in vitro relative to the volume in vivo may be influential. Therefore, clot lysis experiments were performed under three conditions: (1) a control plasma volume of 2 ml, (2) an increased plasma volume of 5 ml, and (3) 2 ml plasma with 500 µg/ml C1-inhibitor. Unlabeled blood clots were used for those experiments and the time used to lyse 100% blood clots was determined to be 75-80 minutes in all three conditions tested. In the standard 2 ml plasma volume, the tPA-M5 combination degraded 70% of fibrinogen, reflecting the rapid tcM5 generation rate by plasmin (FIG. 8). When C1-inhibitor was added, fibrinogenolysis was reduced to 45%, with 55% remaining fibrinogen (FIG. 8). A similar effect was observed in 5 ml plasma volume, probably reflecting dilution of tcM5 in the immediate clot environment (FIG. 8). This volume effect suggests that fibrinogenolysis by the tPA-M5 combination may be further attenuated in vivo where the plasma volume to clot ratio is considerably greater.

The more modest effect of C1-inhibitor when compared to FIG. 2D, are related to the more rapid fibrin-dependent plasmin generation induced by the tPA-M5 combination compared with M5 monotherapy. It has been verified by additional studies that the C1-inhibitor's ability to inhibit fibrinogenolysis by the tPA-M5 combination is reduced when compared to its ability to inhibit fibrinogenolysis by M5 alone. C1-inhibitor is a relatively slow inhibitor and thus is less able to quench the more rapidly generated tcM5 from the more rapid fibrinolysis achieved by the tPA-M5 combination. Higher concentration of C1-inhibitor might be needed to sufficiently quench tcM5 generated from the tPA-M5 combination.

Figure 5A:
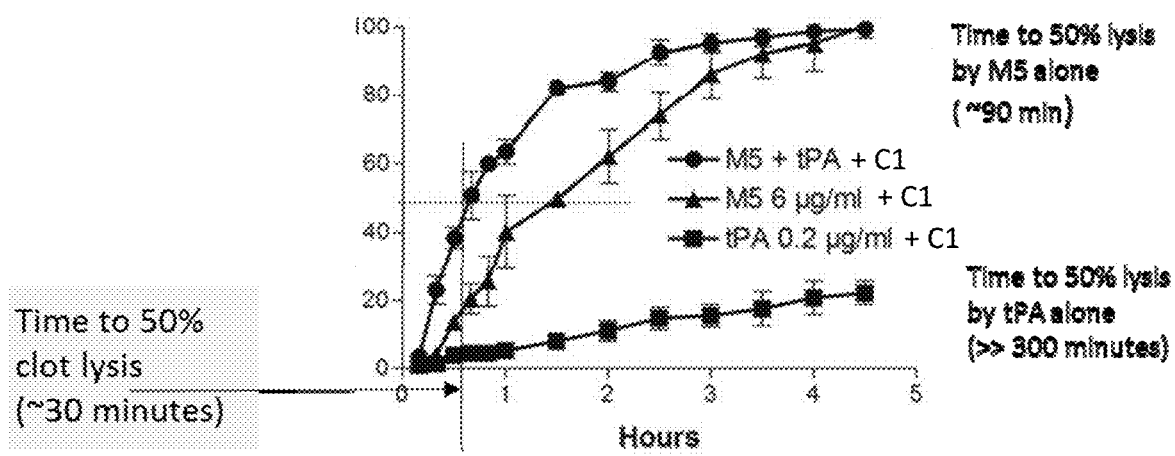
FIG. 5A is a line graph showing maximum clot lysis rate by a combination of tPA (0.2 µg/ml) and M6 (6 µg/ml) in addition to C1-inhibitor (750 µg/ml). The addition of C1-inhibitor to the combination did not inhibit lysis, however it did inhibit lysis by tPA alone.
Figure 5B:
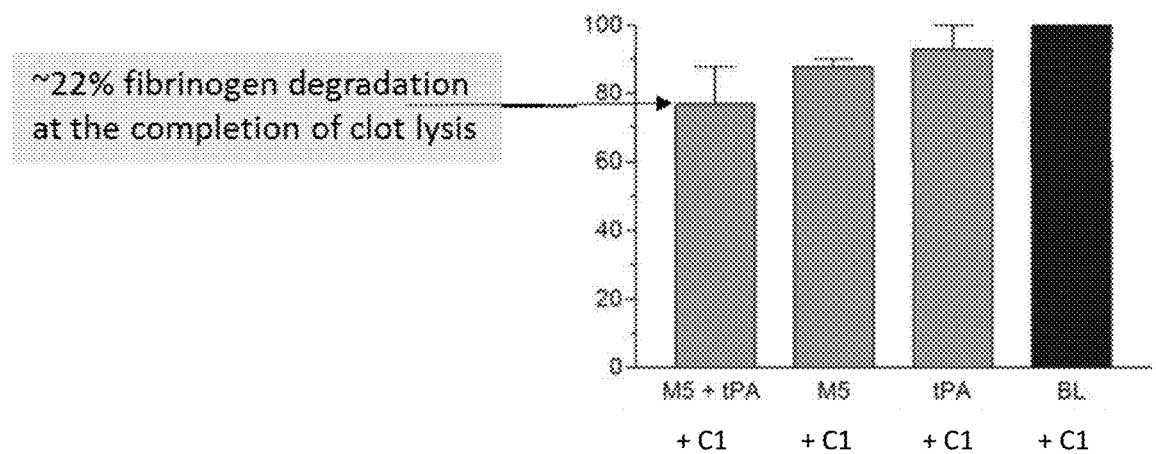
FIG. 5B is a bar graph showing the remaining plasma fibrinogen at the end of clot lysis, expressed as percentage of baseline (BL) fibrinogen. The C1-inhibitor attenuated fibrinogenolysis.

The results of representative clot lysis experiments are shown in FIG. 5A, using the combination (0.2 µg/ml tPA+6 µg/ml M5) (circle) in addition to C1-inhibitor. C1-inhibitor (750 µg/ml) was added 30 minutes after the addition of the activators. As shown in FIG. 5A, this did not inhibit lysis (circles), which on average was shortened to approximately 30 minute, but did inhibit lysis by tPA alone (squares). FIG. 5B shows the plasma fibrinogens at the end of lysis, expressed as percentage baseline (BL) fibrinogen. As shown in FIG. 5B, the C1-inhibitor attenuated fibrinogenolysis. All experiments were performed in triplicate.

Fibrinogenolysis by the tPA-M5 Combination in the Absence of a Clot

Figure 9:
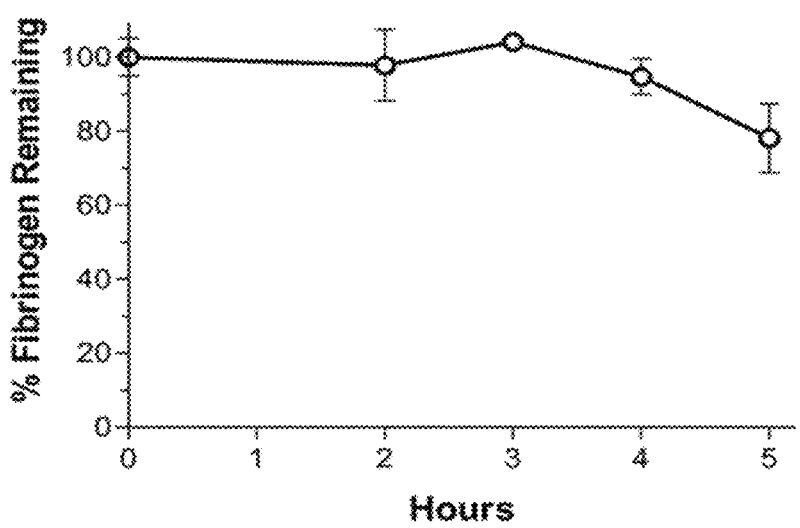
FIG. 9 is a line graph showing that in the absence of a blood clot, no fibrinogenolysis by the combination of 0.2 µg/ml tPA and 6 µg/ml M5 occurred for at least 3 hours, which suggests that in the absence of a clot in vivo the combination would also be inactive.

To test the effect of the tPA-M5 combination on fibrinogenolysis in the absence of a blood clot, the combination of 0.2 µg/ml of tPA plus 6 µg/ml of M5 was incubated with plasma at 37° C. and samples were taken for fibrinogen determination after 2-5 hours. As shown in FIG. 9, there was no fibrinogenolysis for at least 3 hours, well beyond the duration of therapeutic thrombolysis. These findings indicate that the plasmin generation induced by the tPA-M5 combination was fibrin-dependent and that in the absence of a blood clot, this fibrinolytic combination does not induce plasminogen activation.

Example 2. Thrombolysis In Vivo by a Combination of tPA and M5

Male, mongrel dogs weighing 10-15 kg are anesthetized with pentobarbital sodium and maintained breathing room air. Blood clots are formed from 1 ml of native whole dog blood as described in U.S. Pat. No. 7,074,401, to which radiolabeled fibrinogen (1.9 µCi, 0.75 mCi/mg protein) and thrombin (10 units) are added. After 20 minutes, the clots are washed with saline three times and then cut into small (about 1 mm$^3$) pieces and injected through a 16-gauge needle into the femoral vein. After 15 minutes, a blood sample is obtained from a cannula in the contralateral femoral vein for the measurement of baseline radioactivity.

The dogs are divided into four groups and injected with (1) saline, (2) a bolus of 2-5 mg of tPA, (3) intravenous infusion of M5 (20 µg/kg/min) for 60 minutes, or (4) a bolus of 2-5 mg of tPA followed by intravenous infusion of M5 (20 µg/kg/min) for 60 minutes. At intervals during the infusions, blood samples were obtained and measured for radioactivity and fibrinogen. Time used to lyse blood clots is determined and compared among the four groups.

Example 3. Characterization of C1 Inhibitor and M5 in a Rat Model of Intracerebral Hemorrhage (ICH)

The purpose of this study was to investigate the effect of M5 on intra-cerebral hemorrhage (ICH) volume.

Twenty adult, male Sprague-Dawley rats were used for the study. Rats were randomly selected for use on surgical days. Rats were given a unique identification number by tail marking Immediately prior to initiation of surgery Cefazolin Sodium intraperitoneal injection (40 mg/kg; Hospira 101C049) and Buprenorphine subcutaneous (1 mg/kg; Reckitt Benckiser, 219202) were administered to the animals. While the rats were under isoflurane anesthesia (1.5% to 2%) with spontaneous respiration in a nitrous oxide/oxygen mixture (2:1), a small burr hole was drilled, and a 30-gauge 10 microliter microinjection needle (Hamilton, 700 series) was slowly lowered into the right striatum at the following coordinates from the bregma: 0.0 mm anterior, 3 mm lateral, and 6 mm depth. During a period of 3 minutes, 3 microliters of saline containing 0.45 U collagenase VII-S (Sigma, St. Louis, Mo.) was injected. The needle was left in place for 2 minutes and then slowly removed over 5 minutes. Afterward, the scalp was stapled closed, and the rats were allowed to recover. The whole surgical procedure lasted about 20 minutes for each rat. A heating pad (37±1° C.) is used to maintain animal body temperatures.

The C1 inhibitor and the test article (M5) were formulated prior to dosing. Test solutions were kept on ice during the daily usage. The remaining unused solutions were kept at −20° C. Immediately after a bolus at 4 mL/kg (IV), animals were dosed by intravenous infusion (over 30 minutes), starting at 15 minutes following ICH at 4 mL/kg. At 2 hours after the beginning of infusion, animals were humanely killed under isoflurane in 100% $N_2O$ inhalation. Brains were removed and cut in slices according to a 2-mm rat brain matrix. Under standardized conditions, images of the brain slices were taken with a digital camera. Hematoma size was calculated by ImageJ software (available online at rsb.info.nih.gov/ij).

Two hours after hemorrhage induction, rats were sacrificed under deep (5%) isoflurane anesthesia (100% N2O). Brains were removed and placed in phosphate-buffered saline (PBS) on ice. Brains were sliced into 7 sections of 2 mm each and photographed for a visual assessment of the hematoma. A histological assessment was not conducted on the individual sections. Hemoglobin content was determined as a quantitative measurement of hemorrhagic volume. The hemorrhaged side (inclusive of all 7 sections) was isolated from the normal side and placed into 1.5 mL of cold PBS. After 30 seconds of homogenization (manually with a Polytron PT2100), ultrasound was applied for 1 minute to lyse erythrocytic membranes. After centrifugation for 30 minutes (13000 rpm, 4° C.), 200 μL of supernatant was added to 800 μL of Drabkins reagent (Sigma, St. Louis, Mo.) and allowed to sit for 10 minutes at room temperature. With use of a photometer, absorption rates were determined at 540 nm, and hemorrhagic blood volumes were calculated for the injured half of the brain on the basis of a standard curve. The standard curve was generated by using eight naïve brain hemispheres from age and weight matched (to the average study subject). These naïve brain hemispheres were spiked with pooled blood from the same individuals at increasing volumes from 0 to 192 μL. Statistical significance was assessed by analysis of variance (ANOVA).

The timing at which the size of the hemorrhage was measured (2 hours post hemorrhage induction) was determined from previous work optimized at Biotrofix.

Rats were dosed as described with a bolus (4 ml/kg) of vehicle (saline) (4 ml/kg) followed immediately with a 30 minute infusion of vehicle, or a bolus of C1 inhibitor (200 U/4 ml/kg) followed immediately with a 30 minute infusion of M5 (10 mg/4 ml/kg) at fifteen minutes post-ICH.

Clinical Observations and Survival

All animals survived the study period for this study Animal #24 was not included for the analysis as there was insufficient hemorrhage induced in this animal to be included.

Histological Determination of Hemorrhage Volume

M5 (immediately) following a C1 inhibitor bolus injection was studied in a rat model of ICH. In this model, an intracerebral hemorrhage was induced by injection of collagenase into the right striatum of the brain. Fifteen minutes post-injury M5 (at a dose of 10 mg/4 ml/kg) or vehicle was administered by a 30 minute intravenous infusion immediately following bolus injections as described above. No significant difference (p=0.6899) was determined between the animals dosed with C1inh/M5 and those dosed with saline/saline (FIG. 1).

Direct Hematoma Volume

Figure 10A:
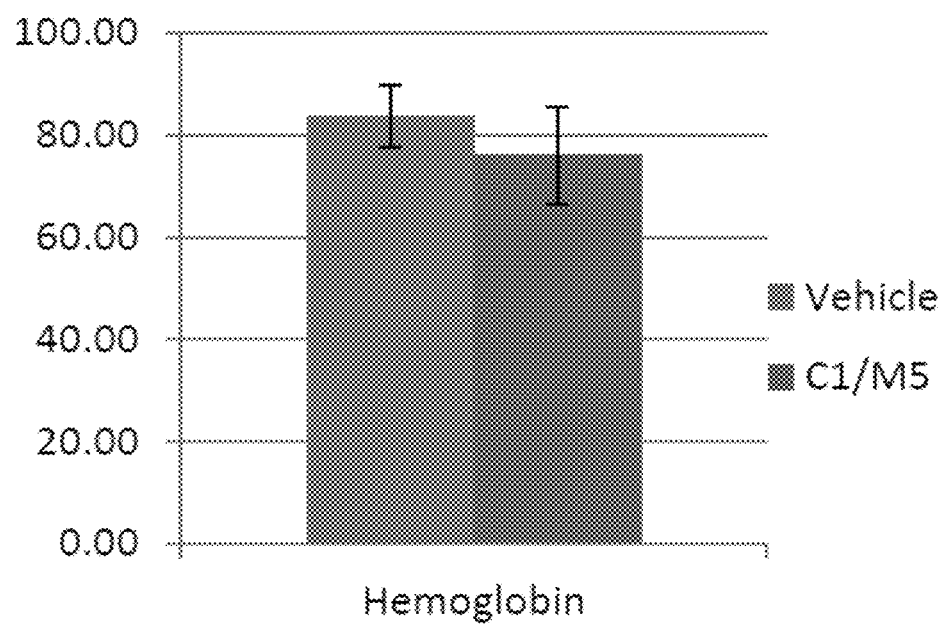
FIG. 10A is a bar graph showing the hematoma volume following intracerebral hemorrhage in a rat model. Hematoma volume was measured by hemoglobin content at 2 hours post dosing. No significant difference (p=0.5194) was determined between the animals dosed with C1 inhibitor/M5 and those dosed with saline/saline. The C1-inhibitor was included since the rat is missing this inhibitor of M5/UK.
Figure 10B:
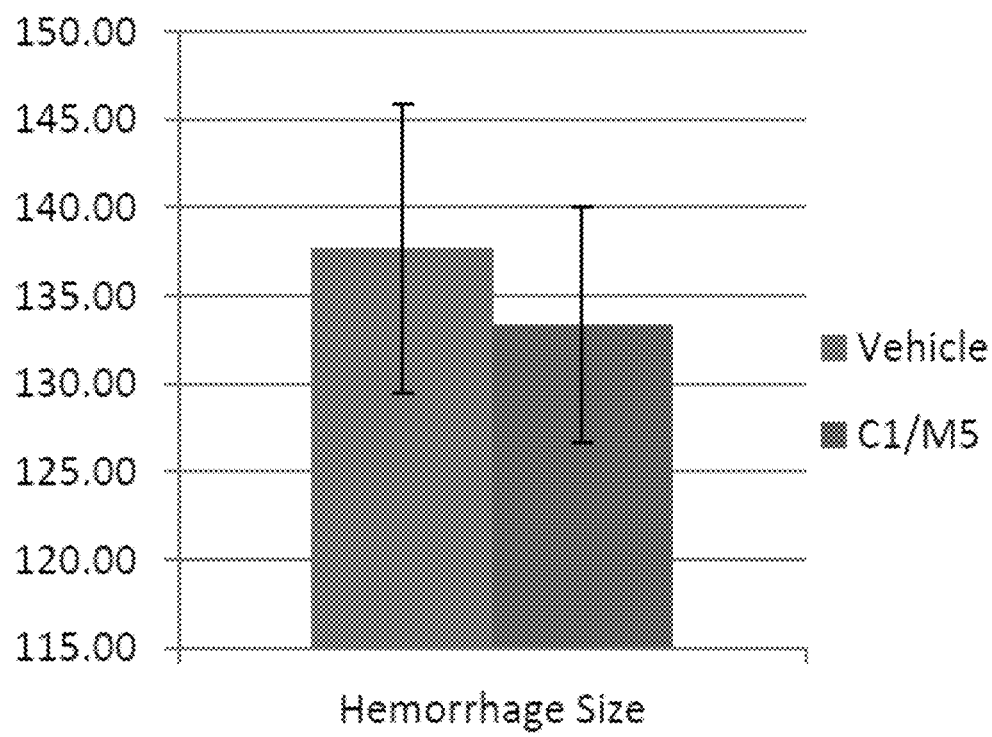
FIG. 10B is a bar graph showing the histological determination of hemorrhage volume following intracerebral hemorrhage in a rat model. No significant difference (p=0.6899) in hemorrhage volume was determined between the animals dosed with C1 inhibitor/M5 and those dosed with saline/saline.

As with the histological determination for hemorrhage volume, no significant difference (p=0.5194) was determined between the animals dosed with C1inh/M5 and those dosed with saline/saline (FIGS. 10A and 10B). FIG. 10A is a bar graph showing the hematoma volume following intracerebral hemorrhage in a rat model. Intracerebral hemorrhage was induced by stereotactic injection of collagenase. Rats were dosed at 15 minutes post injury with a C1inhibitor bolus injection followed immediately with a 30 minute infusion of M5 (at a dose of 10 mg/4 ml/kg). Hematoma volume was measured by hemoglobin content at 2 hours post dosing. No significant difference (p=0.5194) was determined between the animals dosed with C1inh/M5 and those dosed with saline/saline.

FIG. 10B is a bar graph showing the histological determination of hemorrhage volume following intracerebral hemorrhage in a rat model. Intracerebral hemorrhage was induced by stereotactic injection of collagenase. Rats were dosed at 15 minutes post injury with a C1inhibitor bolus injection followed immediately with a 30 minute infusion of M5 (at a dose of 10 mg/4 ml/kg). No significant difference (p=0.6899) in hemorrhage volume was determined between the animals dosed with C1inh/M5 and those dosed with saline/saline.

In this rat model of collagenase induced intracerebral hemorrhage, the administration of C1 inhibitor/M5 administered 15 minutes post ICH induction did not differ in hematoma volume or hemorrhage size relative to saline/saline treated animals. Thus, M5 did not induce or augment bleeding in this stroke model and thus should be safe to use in bleeding events such as hemorrhagic stroke.

Example 4. Clinical Trial of a Combination of tPA and M5

Healthy male subjects, aged between 18 and 35 years inclusive, and with a body weight of at least 60 kg and a body mass index (BMI) between 18.5 and 25 $kg/m^2$ inclusive are enrolled in the clinical trial. The subjects have normal endogenous C1-inhibitor, α2-antiplasmin, and fibrinogen levels, a negative serology for HIV, HBsAg, and HCV, and a negative test for alcohol and drugs of abuse at screening and on study day 1. The subjects cannot have clinically significant abnormalities.

A subject is not included if he fulfils one or more of the following criteria: (1) the subject has a known or suspected inherited, congenital, or acquired disease or condition that affects the haemostatic or coagulation pathways or that is associated with an increased bleeding tendency; (2) the subject has a reasonable chance of developing a clinically significant bleeding event or a bleeding event that may go undetected for a considerable amount of time during the study, for example, the subject (a) has undergone major (internal) surgery or trauma within the last three months of the anticipated dosing day, (b) has an intestinal or cerebral vascular malformation, or (c) has participated in high impact contact sports, such as kick-boxing, within two weeks of the anticipated dosing day; (3) the subject has received any systemically absorbed drug or substance (including prescription, over-the-counter, or alternative remedies) that is not permitted by this protocol prior to dosing without undergoing a wash-out period of at least seven times the elimination half-life of the product; (4) the subject has smoked tobacco in any form within three months of dosing, or has ever smoked more than five cigarettes per day (or equivalent) on average; (5) the subject has received blood or plasma derivatives in the year preceding the administration day; (6) the subject has lost blood or plasma outside the limits of the local blood donation service (i.e. Sanquin) three months prior to dosing; (7) the subject has a known hypersensitivity to any of the investigational material or related compounds; (8) the subject has a history of severe hypersensitivity or of an allergy with severe reactions; (9) the subject has a history of substance abuse, including caffeine, tobacco, and alcohol; (10) the subject has a condition or demonstrates an attitude that in the opinion of the investigator might jeopardize the subject's health or well-being, or the scientific integrity of the study results; (11) the subject is mentally or legally incapacitated to provide informed consent.

The enrolled subjects are randomly allocated to one of the following treatment arms:

(1) Injection of a bolus of 2.5 mg of tPA followed by intravenous infusion of an mproUK, e.g., M5, for 60-90 minutes at approximately 80 mg/hour (50% of the monotherapy dose);

(2) Injection of a bolus of 2.5 mg of tPA followed by intravenous infusion of a placebo for 60-90 minutes;

(3) Injection of a placebo bolus followed by intravenous infusion of an mproUK, e.g., M5, for 60-90 minutes at approximately 160 mg/hour; or (4) Injection of a bolus of 2.5 mg of tPA followed by a C1-inhibitor (Berinert®) bolus (e.g. 1000 EU (2 vials)), and intravenous infusion of an mproUK, e.g., M5, for 60-90 minutes at approximately 80 mg/hour (50% of the monotherapy dose).

The dose for an mproUK ranges from 60-120 mg/hour. The C1-inhibitor bolus consists of 25-100 U/kg of Berinert® (based on body weight of the subject). This study ends either when plasminaemia occurs or when sufficient data has been gathered.

Based on data gathered from this study, the overall safety and tolerability of the combination of tPA and mproUK such as M5 are evaluated. The effect of a mini-dose of tPA on mproUK-induced coagulation changes are assessed. The effect of a single dose of C1-inhibitor on the overall safety and tolerability of tPA-mproUK combination and its effect on tPA-mproUK-induced coagulation changes are assessed.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating a human subject with symptoms of a stroke, the method comprising:
   (a) identifying a human subject who potentially had a stroke by observing a sudden onset of one-sided paralysis without determining the cause of the stroke; and
   (b) administering to the human subject a bolus of a first composition comprising 1 mg to less than 5 mg of tissue plasminogen activator (tPA) followed by an intravenous infusion of a second composition comprising a human pro-urokinase mutant (mproUK) infused over 60 to 90 minutes at a rate of 60 to 120 mg/hour, wherein the human pro-urokinase mutant comprises a substitution of histidine for lysine at amino acid position 300 (Lys300→His) of human pro-urokinase (SEQ ID NO:1), and
   wherein clot lysis is achieved in the human subject with less than about 30 percent fibrinogen degradation in the human subject's blood.

2. The method of claim 1, wherein clot lysis is confirmed as having been achieved by a lysis of about 50% of the mass of at least one clot in the human subject achieved within 75 minutes of the administration of the bolus of tPA followed by the infusion of human mproUK.

3. The method of claim 1, wherein the bolus comprises 2 to 4.5 mg of tPA.

4. The method of claim 3, wherein the bolus comprises 2 to 4.0 mg of tPA.

5. The method of claim 1, wherein the second composition is administered as an intravenous infusion at a rate of 60-90 mg/hour of the human mproUK for 60-90 minutes.

6. The method of claim 5, wherein the second composition is administered as an intravenous infusion at a rate of 60-80 mg/hour of the human mproUK for 60 minutes.

7. The method of claim 1, wherein the administration of the second composition begins within five minutes after the administration of the first composition.

8. The method of claim 1, wherein the first composition and the second composition together lyse 50% of a mass of at least one blood clot in the subject in less than one hour.

* * * * *

SEQUENCE LISTING

```
<160> NUMBER OF SEQ ID NOS: 1

<210> SEQ ID NO 1
<211> LENGTH: 411
<212> TYPE: PRT
<213> ORGANISM: Homo sapiens

<400> SEQUENCE: 1

Ser Asn Glu Leu His Gln Val Pro Ser Asn Cys Asp Cys Leu Asn Gly
1               5                   10                  15

Gly Thr Cys Val Ser Asn Lys Tyr Phe Ser Asn Ile His Trp Cys Asn
            20                  25                  30

Cys Pro Lys Lys Phe Gly Gly Gln His Cys Glu Ile Asp Lys Ser Lys
        35                  40                  45

Thr Cys Tyr Glu Gly Asn Gly His Phe Tyr Arg Gly Lys Ala Ser Thr
    50                  55                  60

Asp Thr Met Gly Arg Pro Cys Leu Pro Trp Asn Ser Ala Thr Val Leu
65                  70                  75                  80

Gln Gln Thr Tyr His Ala His Arg Ser Asp Ala Leu Gln Leu Gly Leu
                85                  90                  95

Gly Lys His Asn Tyr Cys Arg Asn Pro Asp Asn Arg Arg Arg Pro Trp
            100                 105                 110

Cys Tyr Val Gln Val Gly Leu Lys Pro Leu Val Gln Glu Cys Met Val
        115                 120                 125

His Asp Cys Ala Asp Gly Lys Lys Pro Ser Ser Pro Pro Glu Glu Leu
    130                 135                 140

Lys Phe Gln Cys Gly Gln Lys Thr Leu Arg Pro Arg Phe Lys Ile Ile
145                 150                 155                 160

Gly Gly Glu Phe Thr Thr Ile Glu Asn Gln Pro Trp Phe Ala Ala Ile
                165                 170                 175
```

```
Tyr Arg Arg His Arg Gly Gly Ser Val Thr Tyr Val Cys Gly Gly Ser
            180                 185                 190

Leu Ile Ser Pro Cys Trp Val Ile Ser Ala Thr His Cys Phe Ile Asp
        195                 200                 205

Tyr Pro Lys Lys Glu Asp Tyr Ile Val Tyr Leu Gly Arg Ser Arg Leu
    210                 215                 220

Asn Ser Asn Thr Gln Gly Glu Met Lys Phe Glu Val Glu Asn Leu Ile
225                 230                 235                 240

Leu His Lys Asp Tyr Ser Ala Asp Thr Leu Ala His His Asn Asp Ile
                245                 250                 255

Ala Leu Leu Lys Ile Arg Ser Lys Glu Gly Arg Cys Ala Gln Pro Ser
            260                 265                 270

Arg Thr Ile Gln Thr Ile Cys Leu Pro Ser Met Tyr Asn Asp Pro Gln
        275                 280                 285

Phe Gly Thr Ser Cys Glu Ile Thr Gly Phe Gly Lys Glu Asn Ser Thr
    290                 295                 300

Asp Tyr Leu Tyr Pro Glu Gln Leu Lys Met Thr Val Val Lys Leu Ile
305                 310                 315                 320

Ser His Arg Glu Cys Gln Gln Pro His Tyr Tyr Gly Ser Glu Val Thr
                325                 330                 335

Thr Lys Met Leu Cys Ala Ala Asp Pro Gln Trp Lys Thr Asp Ser Cys
            340                 345                 350

Gln Gly Asp Ser Gly Gly Pro Leu Val Cys Ser Leu Gln Gly Arg Met
        355                 360                 365

Thr Leu Thr Gly Ile Val Ser Trp Gly Arg Gly Cys Ala Leu Lys Asp
    370                 375                 380

Lys Pro Gly Val Tyr Thr Arg Val Ser His Phe Leu Pro Trp Ile Arg
385                 390                 395                 400

Ser His Thr Lys Glu Glu Asn Gly Leu Ala Leu
                405                 410
```